US012357120B2

(12) United States Patent
Kiriseko et al.

(10) Patent No.: US 12,357,120 B2
(45) Date of Patent: Jul. 15, 2025

(54) FLAVOR DISPENSER APPARATUS

(71) Applicant: JAPAN TOBACCO INC., Tokyo (JP)

(72) Inventors: Akito Kiriseko, Tokyo (JP); Yui Nakayama, Tokyo (JP); Minoru Sakurai, Tokyo (JP); Sho Tanaka, Tokyo (JP); Tatsuya Narita, Tokyo (JP); Ryousuke Suda, Kadoma (JP); Shinichi Fukushima, Kadoma (JP); Seiji Yoshimura, Kadoma (JP); Hidenori Fukuoka, Kadoma (JP); Kazuo Mori, Kadoma (JP)

(73) Assignee: JAPAN TOBACCO INC., Tokyo (JP)

( * ) Notice: Subject to any disclaimer, the term of this patent is extended or adjusted under 35 U.S.C. 154(b) by 851 days.

(21) Appl. No.: 17/578,009

(22) Filed: Jan. 18, 2022

(65) Prior Publication Data

US 2022/0132933 A1 May 5, 2022

Related U.S. Application Data

(63) Continuation of application No. PCT/JP2020/023567, filed on Jun. 16, 2020.

(30) Foreign Application Priority Data

Jul. 19, 2019 (JP) ................................ 2019-134055

(51) Int. Cl.
*A61L 9/03* (2006.01)
*A23B 4/052* (2006.01)
(Continued)

(52) U.S. Cl.
CPC .............. *A47J 31/44* (2013.01); *A23B 4/052* (2013.01); *A61L 9/035* (2013.01); *B05B 7/1686* (2013.01); *B05B 7/1693* (2013.01); *A61L 9/03* (2013.01)

(58) Field of Classification Search
CPC ... A61L 9/03; A61L 9/035; A61L 9/02; A23B 4/052; B05B 7/1606; B05B 7/1613; B05B 7/1626; B05B 7/1686; B05B 7/1693
(Continued)

(56) References Cited

U.S. PATENT DOCUMENTS 6,365,211 B1 4/2002 Corrigan
12,128,175 B2 * 10/2024 Bourque .............. A61M 11/042
(Continued)

FOREIGN PATENT DOCUMENTS

CN 109714987 A 5/2019
JP 04221564 A * 8/1992 ............... A61L 9/03
(Continued)

OTHER PUBLICATIONS

Taiwanese Office Action and Search Report dated Jun. 5, 2023 for Application No. 109120401 with an English translation.
(Continued)

*Primary Examiner* — Reginald Alexander
(74) *Attorney, Agent, or Firm* — Birch, Stewart, Kolasch & Birch, LLP

(57) ABSTRACT

There is provided a flavor dispenser apparatus that allows flavored aerosols to be dispensed into a glass, plate, or other dishware during a meal or the like. The flavor dispenser apparatus includes a storage part storing an aerosol-generating liquid, a heating unit having a heater and generating an aerosol by atomizing the aerosol-generating liquid, a liquid delivery unit delivering the aerosol-generating liquid to the heating unit, an aerosol passage having at a distal end thereof an aerosol outlet port, a flavor source holding part provided at an intermediate point in the aerosol passage and holding a flavor source so as to allow passage of the aerosol, and an aerosol-pumping unit transporting the aerosol toward the flavor source holding part and causing the aerosol to pass (Continued)

through the flavor source as well as causing the aerosol flavored by the flavor source to be discharged from the aerosol outlet port.

14 Claims, 25 Drawing Sheets

(51) Int. Cl.
  *A47J 31/44* (2006.01)
  *B05B 7/16* (2006.01)
(58) Field of Classification Search
  USPC .................................................. 392/390, 404
  See application file for complete search history.

(56) References Cited

U.S. PATENT DOCUMENTS

| 2006/0140595 | A1* | 6/2006 | Grabowski | .......... | A61H 33/063 |
| | | | | | 392/386 |
| 2014/0290650 | A1 | 10/2014 | Ivey | | |
| 2017/0319799 | A1 | 11/2017 | Yamada et al. | | |
| 2019/0083670 | A1 | 3/2019 | Zheng et al. | | |
| 2019/0124992 | A1 | 6/2019 | Nakano et al. | | |
| 2019/0217028 | A1 | 7/2019 | Nakano | | |
| 2019/0230992 | A1 | 8/2019 | Blick et al. | | |

FOREIGN PATENT DOCUMENTS

| JP | 2003-502068 A | | 1/2003 | | |
| KR | 20160001140 U | * | 4/2016 | .............. | A61L 9/03 |
| TW | 201813529 A | | 4/2018 | | |
| WO | WO 2016/121143 A1 | | 8/2016 | | |
| WO | WO 2018/002989 A1 | | 1/2018 | | |
| WO | WO 2018/227275 A1 | | 12/2018 | | |

OTHER PUBLICATIONS

International Search Report (PCT/ISA/210) issued in PCT/JP2020/023567 mailed on Aug. 4, 2020.
Extended European Search Report dated Jul. 28, 2023 for Application No. 20844568.4.

* cited by examiner

FLAVOR DISPENSER APPARATUS

CROSS-REFERENCE TO RELATED APPLICATION

The present application is a continuation application of International Application No. PCT/JP2020/023567, filed on Jun. 16, 2020, which claims priority to Japanese Patent Application No. 2019-134055, filed on Jul. 19, 2019. The contents of these applications are incorporated herein by reference in their entirety.

TECHNICAL FIELD

The present invention relates to a flavor dispenser apparatus.

BACKGROUND ART

A smoking technique is known as a technique for imparting a flavor to food or the like by exposing the food to smoke. Smoking is a technique for flavoring food by burning smoking material such as smoke chips or smoke wood with a burner flame or the like to create smoke and by exposing the food to this smoke. In a restaurant or elsewhere, there is a case where a dish poured with liquid nitrogen is served to a customer. Liquid nitrogen has an extremely low boiling point and evaporates at room temperature. Therefore, the use of liquid nitrogen allows a dish to be served with smoke, such as that of sublimating dry ice, to a customer and is suitable for adding a performance aspect.

Another technique is known, whereby a cooking aid agent is sprayed from a compressed aerosol can and applied to cooking equipment to prevent a food material that is being cooked from sticking to the cooking equipment (see, for example, PTL 1).

A dispenser that supplies beverage or vapor is also known (see, for example, PTL 2).

CITATION LIST

Patent Literature

[PTL 1] Japanese Translation of PCT Application No. 2003-502068
[PTL 2] WO 2018/227275

SUMMARY OF INVENTION

Technical Problem

However, smoke produced by the smoking technique mentioned above is already gone by the time the food is served to the user.

In the case where food is served with the use of liquid nitrogen, while the liquid nitrogen may sometimes cause changes in characteristics of the food, the tasteless, odorless liquid nitrogen does not contribute to flavoring of the food.

The present invention was made in view of the circumstances described above, an object thereof being to provide a flavor dispenser apparatus that allows flavored aerosols to be dispensed into a glass, plate, or other dishware during a meal or the like.

Solution to Problem

To solve the problems described above, the flavor dispenser apparatus according to the present invention is characterized to include: a storage part storing an aerosol-generating liquid; a heating unit having a heater that heats the aerosol-generating liquid and generating an aerosol by atomizing the aerosol-generating liquid; a liquid delivery unit delivering the aerosol-generating liquid stored in the storage part to the heating unit; an aerosol passage for the aerosol generated in the heating unit to flow therethrough, the aerosol passage having an aerosol outlet port at a distal end thereof for discharging the aerosol to outside; a flavor source holding part provided at an intermediate point in the aerosol passage and holding a flavor source so as to allow passage of the aerosol flowing through the aerosol passage; and an aerosol-pumping unit transporting the aerosol generated in the heating unit through the aerosol passage toward the flavor source holding part and causing the aerosol to pass through a flavor source in the flavor source holding part as well as causing the aerosol flavored by the flavor source to be discharged from the aerosol outlet port.

The aerosol-pumping unit herein may include a pump or a tank for pneumatic transport of the aerosol generated in the heating unit through the aerosol passage toward the flavor source holding part.

The aerosol-generating liquid may have a vapor pressure of 6.0 kPa (20° C.) or less.

The flavor source may include a solid flavor material.

The flavor source may be a cartridge that includes a flavor case containing a solid flavor material therein and allowing an aerosol to pass therethrough and that is removably mounted in the flavor source holding part.

The flavor case may be made of a transparent or translucent material.

The flavor case may have, at least in part, a mesh structure or a porous structure.

The flavor source may be mounted in the flavor source holding part in a manner visible from outside.

The flavor dispenser apparatus may further include a hand-held housing, as well as a dispenser nozzle for dispensing an aerosol flavored by the flavor source into dishware, the dispenser nozzle having at a distal end thereof the aerosol outlet port formed.

The flavor source may be a cartridge that includes a flavor case containing a solid flavor material therein and allowing an aerosol to pass therethrough and that is removably mounted in the flavor source holding part, and the housing may be provided with a transparent window that makes the flavor source, mounted in the flavor source holding part, visible from outside.

The flavor dispenser apparatus may further include a stationary housing having in an upper part thereof the aerosol outlet port, with a tubular wall standing in an upper part of the housing to divide an aerosol storage part, which stores an aerosol discharged from the aerosol outlet port, from a lateral ambient space of this aerosol storage part.

The solutions by the present invention to the problems can be adopted in any possible combinations.

Advantageous Effects of Invention

The present invention can provide a flavor dispenser apparatus that allows flavored aerosols to be dispensed into a glass, plate, or other dishware during a meal or the like.

DESCRIPTION OF EMBODIMENTS

Embodiments of a flavor dispenser apparatus according to the present invention are now explained with reference to the drawings. It should be noted that, unless otherwise particularly specified, the sizes, materials, shapes, and relative arrangement or the like of constituent elements described in the embodiments are not intended to limit the technical scope of the invention.

Embodiment 1

Figure 1:
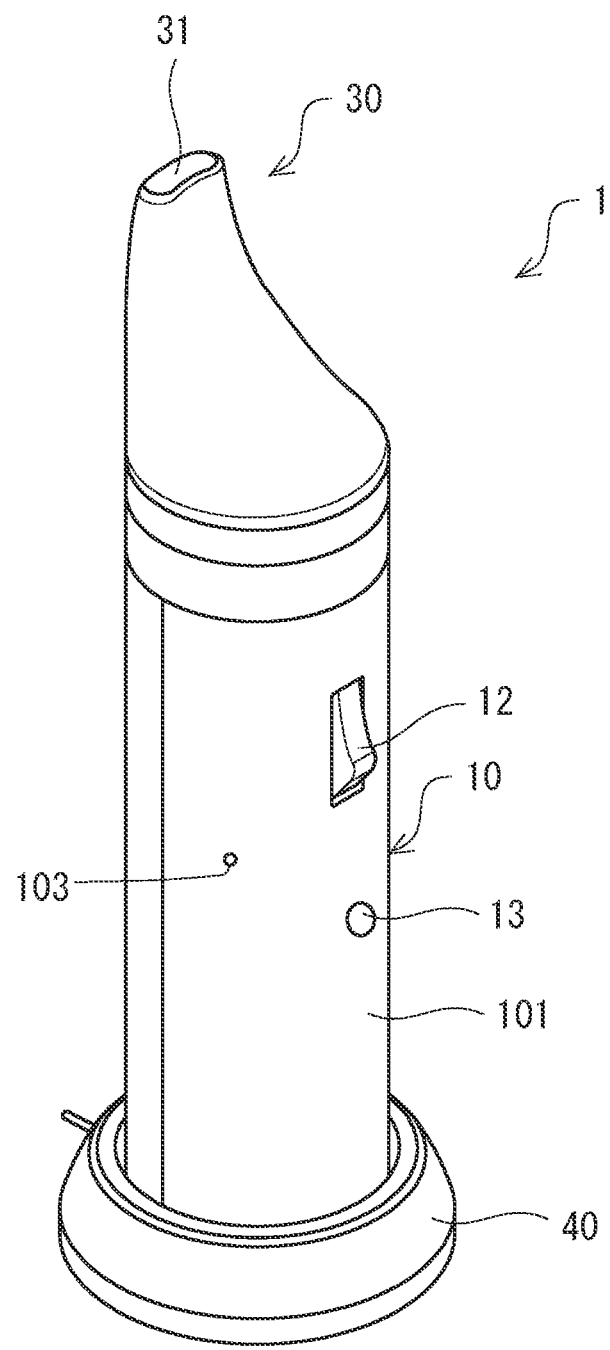
FIG. 1 is a perspective view illustrating an outer appearance of a flavor dispenser apparatus according to Embodiment 1.
Figure 2:
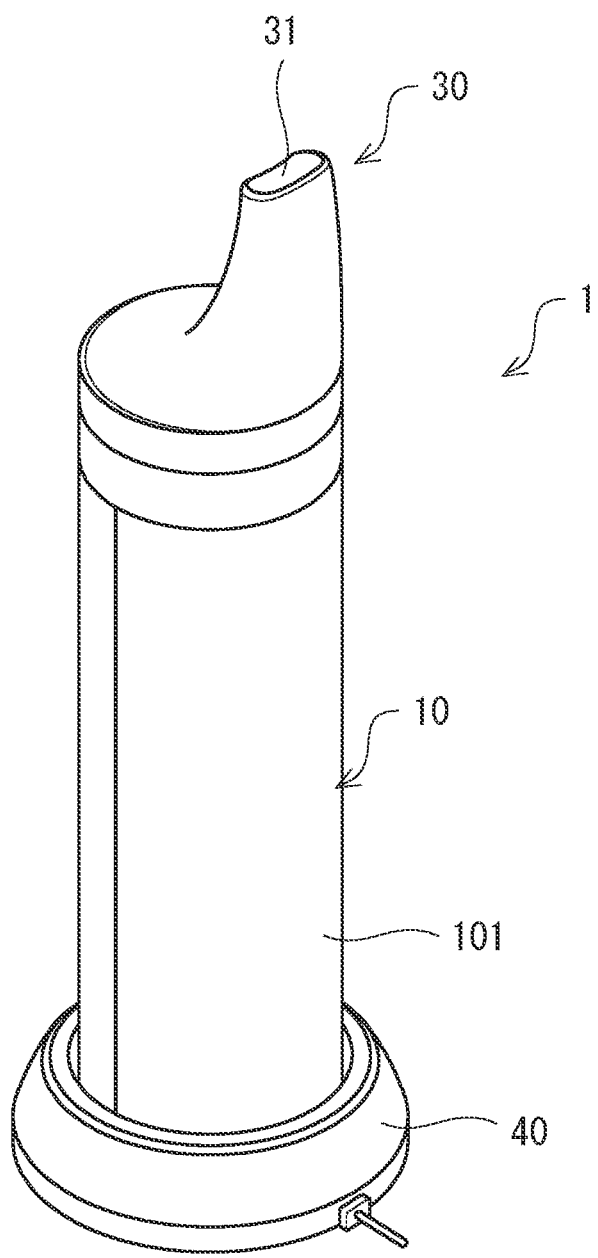
FIG. 2 is a perspective view illustrating an outer appearance of the flavor dispenser apparatus according to Embodiment 1.

FIG. 1 and FIG. 2 are perspective views illustrating an outer appearance of the flavor dispenser apparatus 1 according to Embodiment 1. The flavor dispenser apparatus 1 according to Embodiment 1 is an apparatus for supplying (providing) a flavored aerosol into a glass, plate, or other dishware. The flavor dispenser apparatus 1 includes a hand-held housing 10.

Reference numeral 40 shown in FIG. 1 and FIG. 2 denotes a stand-type cradle (holder) with a power cable. As shown in FIG. 1 and FIG. 2, the flavor dispenser apparatus 1 can be placed on the cradle 40, and in the state in which the flavor dispenser apparatus 1 is placed on the cradle 40, power can be supplied to a battery (power source) of the flavor dispenser apparatus 1 from the power cable. For convenience of explanation, up and down directions referred to herein are defined with reference to the attitude of the flavor dispenser apparatus 1 placed on the cradle 40.

The housing 10 of the flavor dispenser apparatus 1 has a flat bottom, for example, and can stand on its own on a flat surface. On a side face 101 of the housing 10 are provided an operation unit 12 for a user of the flavor dispenser apparatus 1 to operate and a light-emitting element 13. The operation unit 12 is for example an operation lever to be operated by the user, but it may also be an operation button or other operation switches. The light-emitting element 13 is for example a light source such as an LED or electrical light. The light-emitting element 13 is used as an indicator for notifying the user of the operating state of the flavor dispenser apparatus 1, and is controlled to emit light in a predetermined pattern in accordance with the operating state of the flavor dispenser apparatus 1.

As shown in FIG. 1 and FIG. 2, the flavor dispenser apparatus 1 includes a dispenser nozzle 30 at an upper end. An aerosol outlet port 31 opens at a distal end of the dispenser nozzle 30, so that an aerosol that is flavored by a flavor source can be discharged from the aerosol outlet port 31. The flavor dispenser apparatus 1 can dispense this flavored aerosol into a glass, plate, or other dishware by discharging the flavored aerosol from the aerosol outlet port 31 of the dispenser nozzle 30.

Figure 3:
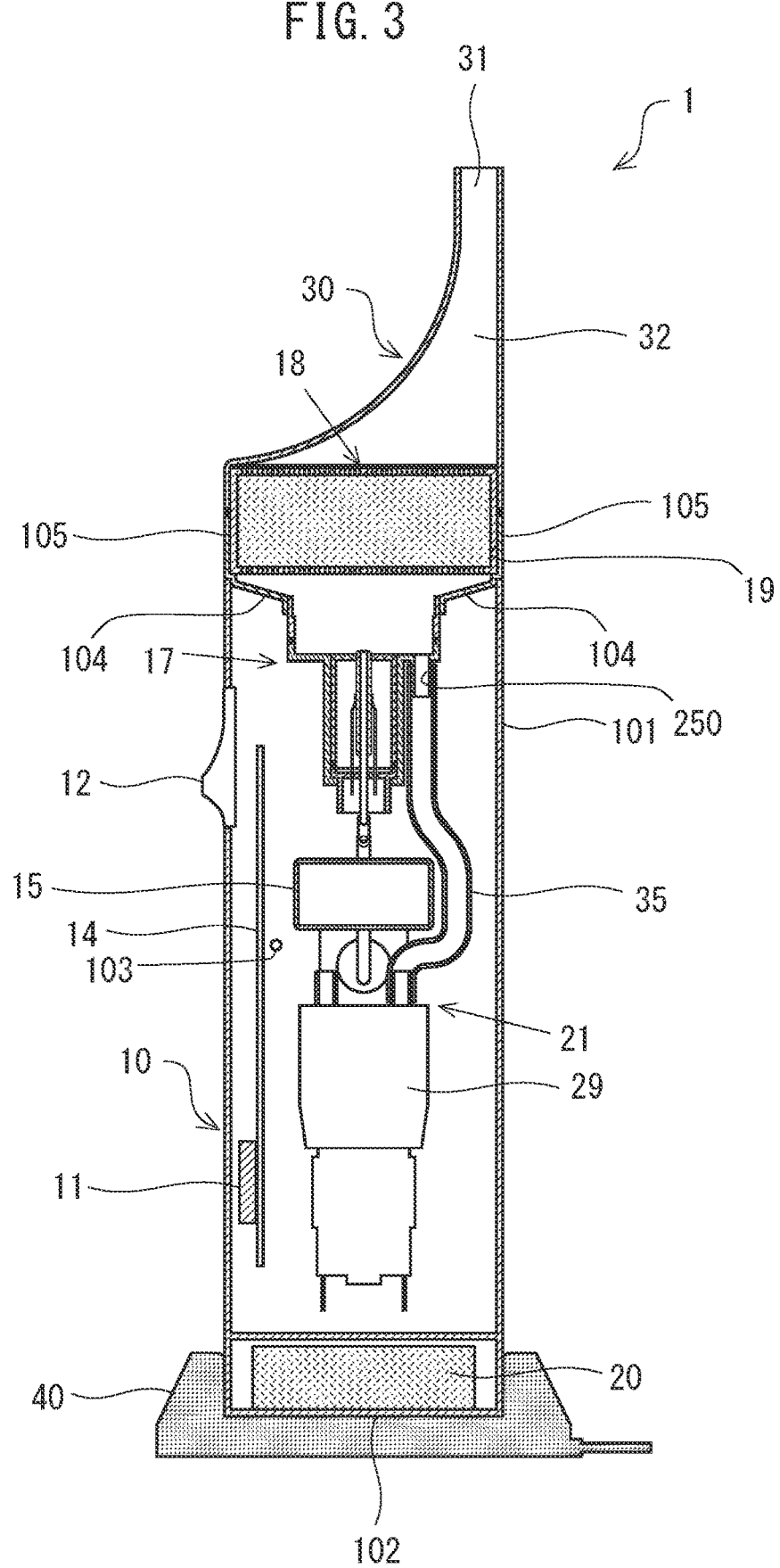
FIG. 3 is a diagram for explaining an internal structure of the flavor dispenser apparatus according to Embodiment 1.

Next, an internal structure of the flavor dispenser apparatus 1 will be described in detail. FIG. 3 is a diagram for explaining the internal structure of the flavor dispenser apparatus 1 according to Embodiment 1. FIG. 3 shows a longitudinal cross section of the flavor dispenser apparatus 1. The housing 10 is a cylindrical casing with a bottom having a hollow structure and accommodates various components that constitute the flavor dispenser apparatus 1 inside. The housing 10 in this embodiment accommodates a control board 14, a storage part 15, a liquid delivery unit 16, a heating unit 17, a flavor cartridge (flavor source) 18, a battery 20, an aerosol-pumping unit 21, and others.

Here, the housing 10 has a cylindrical side face 101 and a circular bottom 102, and its upper end is an open end. The dispenser nozzle 30 is removably attached to the open end of the housing 10. The removable attachment of the dispenser nozzle 30 to the housing 10 is not limited to a particular mechanism, and any known connection means such as thread connection, mating connection, etc. can be used. The housing 10 is not limited to a particular shape. Inside the dispenser nozzle 30 is formed an aerosol passage 32 for the aerosol to flow, and the aerosol outlet port 31 is located at the distal end of the aerosol passage 32.

Figure 4:
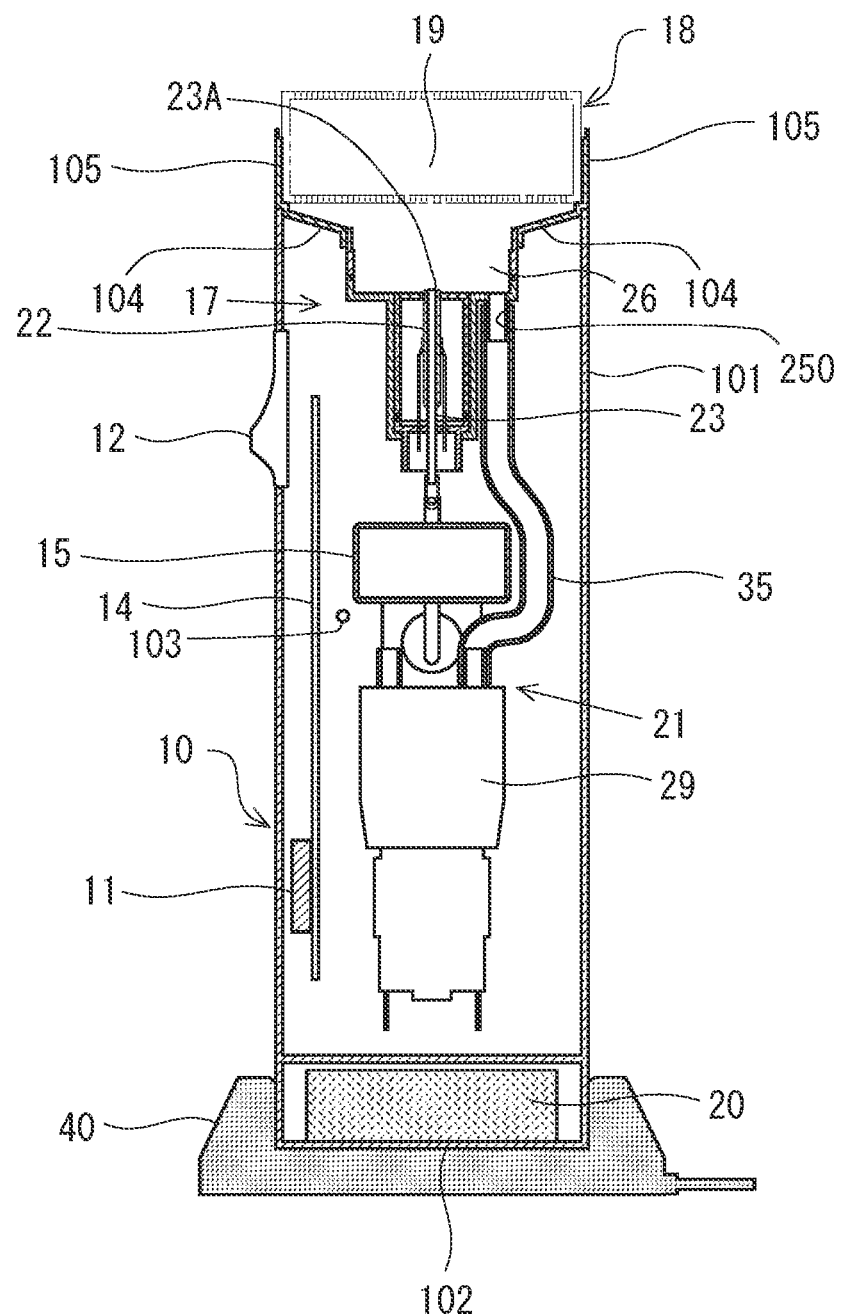
FIG. 4 is a diagram illustrating a state of the flavor dispenser apparatus according to Embodiment 1 in which a dispenser nozzle is separated from a housing.

FIG. 4 shows a schematic illustration of a state of the flavor dispenser apparatus 1 in which the dispenser nozzle 30 is separated from the housing 10. At the upper open end of the housing 10 is formed a flavor source holding part 19, which is a recess that can receive the flavor cartridge (flavor source) 18 shown in FIG. 5, such as to open to outside. The flavor cartridge (flavor source) 18 includes a flavor case 181 and a solid flavor material 182 contained inside this flavor case 181. The flavor material 182 is a material for imparting a flavor to the aerosol generated in the heating unit 17 as will be described later, for which a variety of materials may be used. Examples of applicable flavor material 182 include plant-based raw materials such as pepper, lavender, tobacco, coffee beans, etc., and animal-based raw materials such as bonito flakes. These raw materials for the flavor material 182 may be used as they are, or may be pulverized and/or molded. Alternatively, a flavor component may be extracted from these raw materials and the extracted flavor component may be carried on a carrier.

Figure 5:
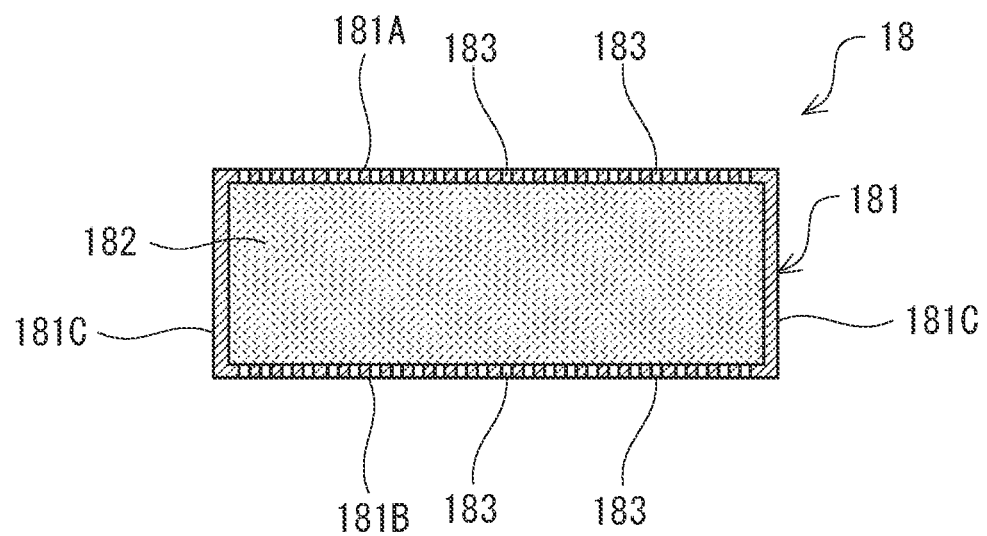
FIG. 5 is a diagram for explaining a flavor cartridge according to Embodiment 1.

The flavor case 181 shown in FIG. 5 is a case having a columnar outer shape with an accommodating space that can contain the flavor material 182 inside, and includes an upper surface 181A, a bottom surface 181B, and a side face 181C. The flavor case 181 is made of a transparent resin, for example, so that the flavor material 182 contained inside is visible from the outside. The flavor case 181 in this embodiment is configured such as to allow an aerosol to pass through, so that, when the aerosol passes through the flavor case 181 of the flavor cartridge 18, the aerosol is flavored by the flavor material 182. The design shown in FIG. 5 has a porous structure, in which numerous air holes 183 are drilled through the upper surface 181A and bottom surface 181B of the flavor case 181 so that the aerosol can pass through the flavor case 181 by flowing through the bottom surface 181B and upper surface 181A. The upper surface 181A and bottom surface 181B of the flavor case 181 may have a mesh structure instead of the porous structure. More particularly, the flavor case 181 should preferably have at least in part a mesh structure or a porous structure, which allows for favorable passage of the aerosol.

The flavor source holding part 19 of the housing 10 is made up of a transparent window part 105 and a guide wall 104 shown in FIG. 4. The transparent window part 105 forms part of the side face 101 of the housing 10 including the open end and is configured by a cylindrical sleeve member. The guide wall 104 is a wall body extending from near a lower end of the transparent window part 105 toward the inner space of the housing 10, diagonally downward toward the heating unit 17 that is disposed below the flavor source holding part 19. The transparent window part 105 has an inside diameter that is set slightly larger than the diameter of the side face 181C of the flavor case 181 described with reference to FIG. 5, so as to allow smooth mounting of the flavor cartridge 18 to, and removal of the flavor cartridge 18 from, the flavor source holding part 19 by the user.

When the flavor cartridge 18 is accommodated in the flavor source holding part 19, the bottom surface 181B of the flavor case 181 abuts on the guide wall 104 that is disposed inside the housing 10, whereby the flavor cartridge 18 is set in position. The transparent window part 105 of the housing 10, which covers the sides of the flavor source holding part 19, is made of a transparent material (e.g., transparent resin, glass and the like). Therefore, the flavor cartridge 18 held in the flavor source holding part 19 is visible by the user from the outside. In a state in which the dispenser nozzle 30 is attached to the housing 10 of the flavor dispenser apparatus 1, the flavor source holding part 19 communicates with the aerosol passage 32 of the dispenser nozzle 30. The flavor case 181 may be disposable, or may be repeatedly used by the user by replacing the flavor material 182 in the flavor case 181. An optional filter may be provided between the flavor source holding part 19 and the heating unit 17 for preventing the flavor material 182 that has dropped through the mesh structure or porous structure of the flavor case 181 from infiltrating the heating unit 17. This filter may be made of any material as long as it has air permeability.

Next, the battery 20 will be described. The battery 20 is accommodated in the housing 10 on the bottom side. The battery 20 receives a supply of power from the power cable attached to the cradle 40 and is charged by the power supplied from the power cable. The battery 20 supplies power necessary for the operation of the flavor dispenser apparatus 1 to various electronic components of the flavor dispenser apparatus 1. The battery 20 may be a lithium ion battery, for example.

The control board 14 is an electronic circuit substrate having a control circuit for controlling the operation of the flavor dispenser apparatus 1. The control board 14 has a processor and a memory or the like mounted thereon, for example, and may be provided in the form of a microprocessor. A sound component 11 such as a buzzer is also mounted on the control board 14. The sound component 11 may be a piezoelectric buzzer or the like, for example. Note, however, the sound component 11 such as a buzzer need not necessarily be provided in the flavor dispenser apparatus 1 of this embodiment. The processor on the control board 14 controls the power supply from the battery 20 to various electronic components.

Figure 6:
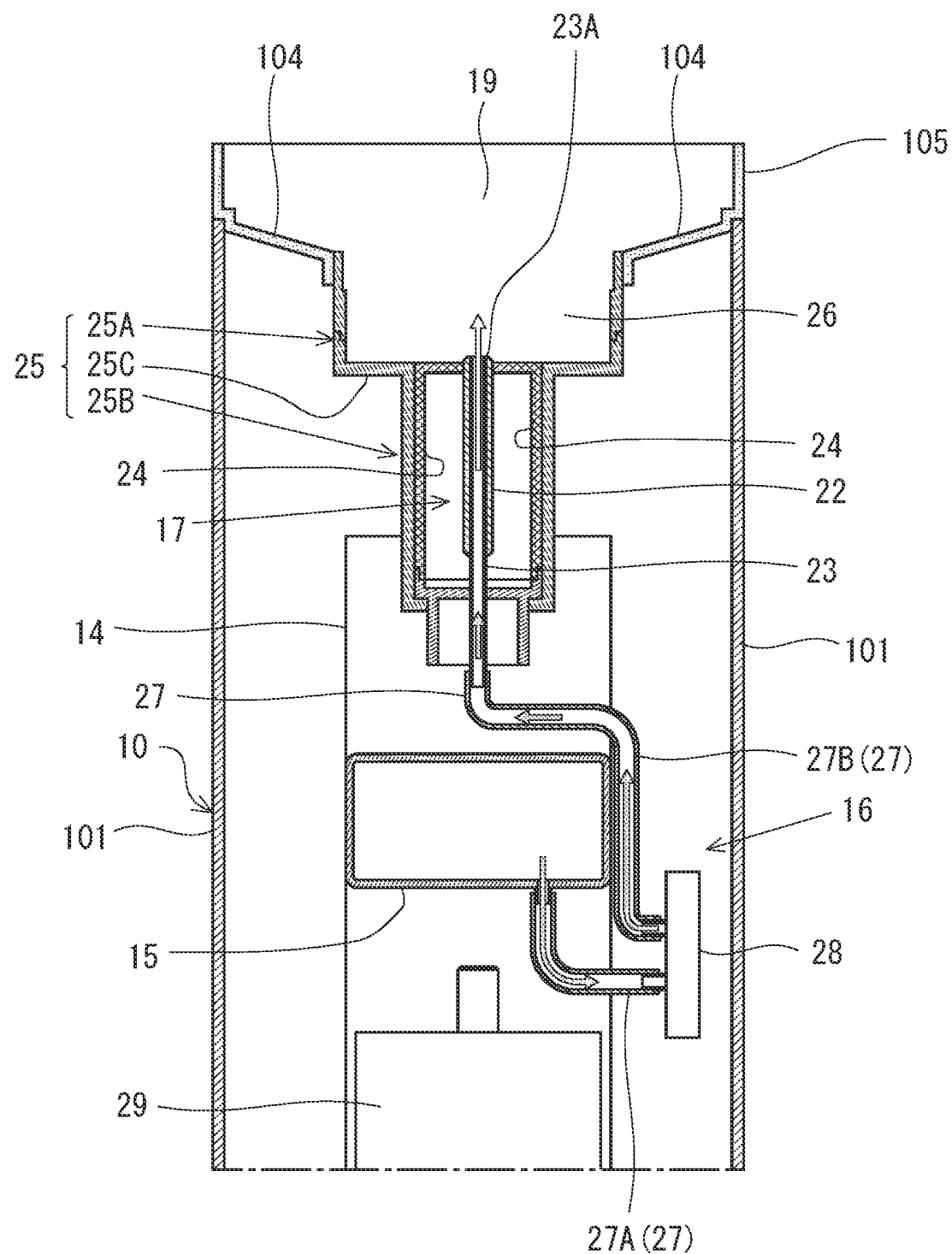
FIG. 6 is a diagram for explaining the details of a storage part, a liquid delivery unit, a heating unit, and an aerosol-pumping unit according to Embodiment 1.
Figure 7:
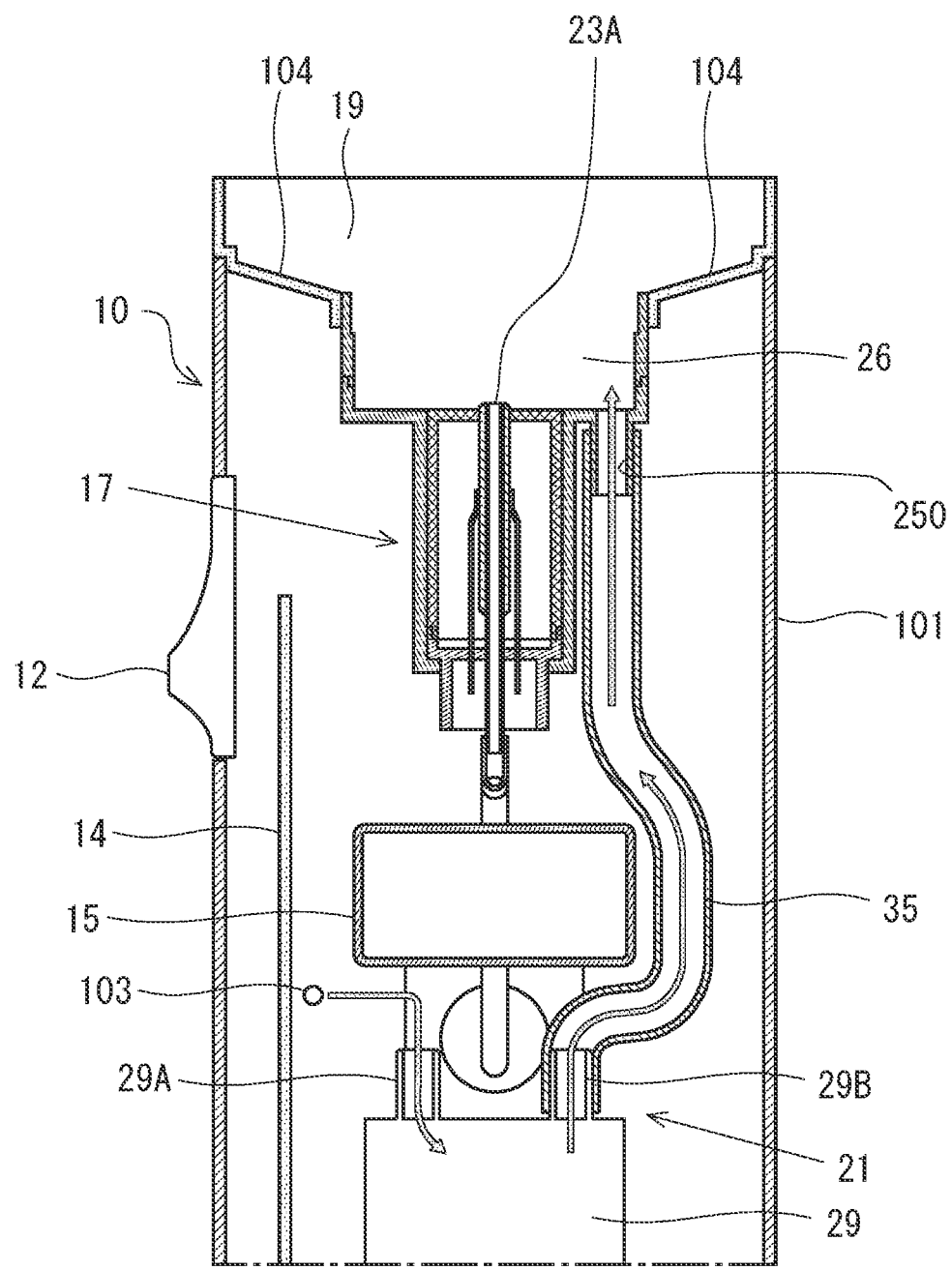
FIG. 7 is a diagram for explaining the details of the storage part, liquid delivery unit, heating unit, and aerosol-pumping unit according to Embodiment 1.
Figure 8:
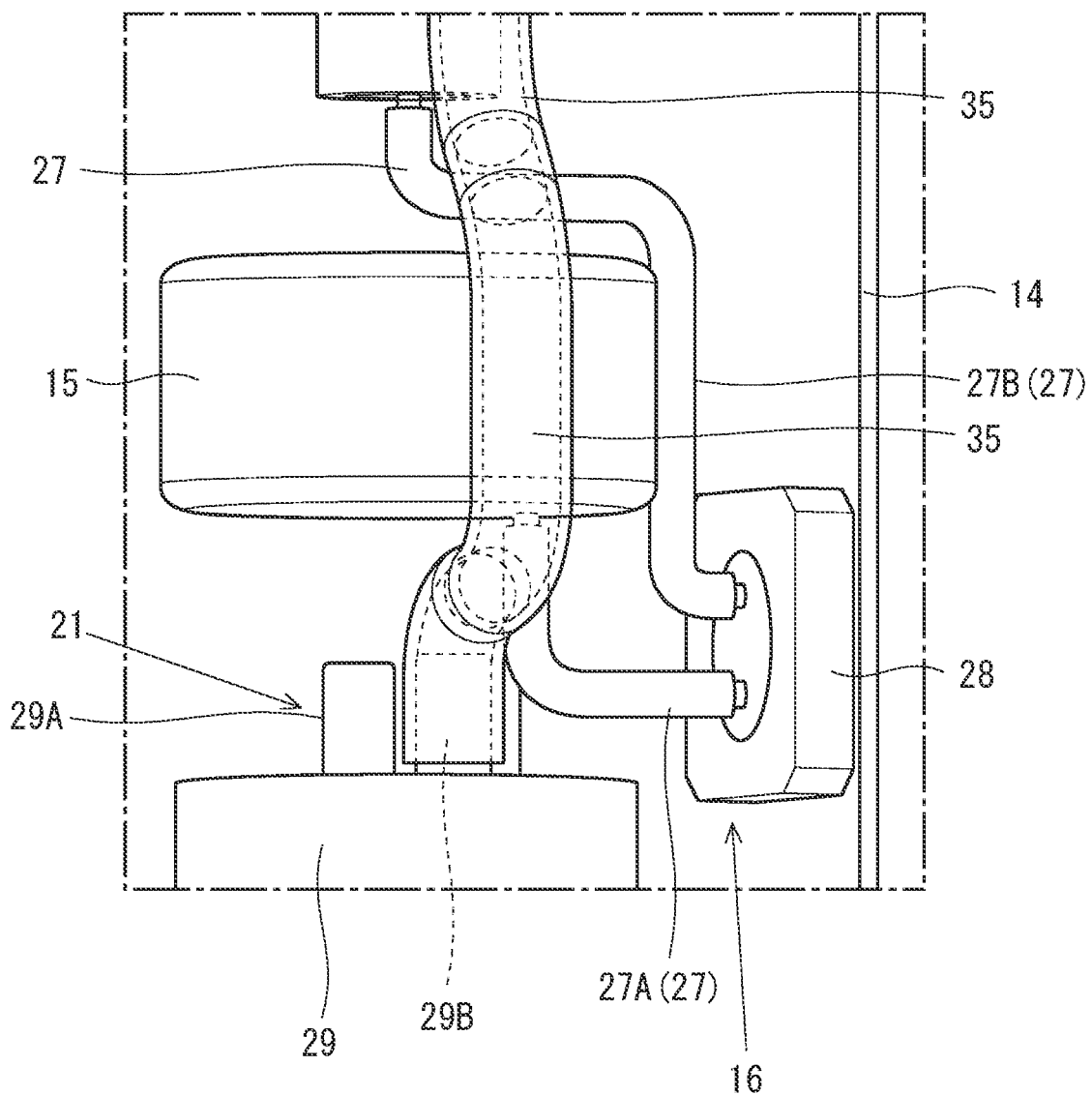
FIG. 8 is a diagram for explaining the details of the storage part, liquid delivery unit, heating unit, and aerosol-pumping unit according to Embodiment 1.

Next, the details of the storage part 15, liquid delivery unit 16, heating unit 17, and aerosol-pumping unit 21 will be described. FIG. 6 to FIG. 8 are diagrams for explaining the details of the storage part 15, liquid delivery unit 16, heating unit 17, and aerosol-pumping unit 21. FIG. 6 to FIG. 8 illustrate the internal structure of some parts of the housing 10.

The storage part 15 is a storage tank that stores an aerosol-generating liquid inside. The aerosol-generating liquid is a liquid based on which an aerosol is generated through atomization by applying heat with a heater to be described later of the heating unit 17. Examples of the aerosol-generating liquid include glycerin, propylene glycol, triethyl citrate, tributyl citrate, jojoba oil, sweet almond oil, olive oil, and the like. The aerosol-generating liquid may also contain a flavor (an essence), water, and the like. The material used for the storage part 15 is not limited to a particular material. For example, PTFE (polytetrafluoroethylene), PP (polypropylene) or the like may be used. The storage part 15 (storage tank) is accommodated in the housing 10 such as to be removable. Therefore, when the aerosol-generating liquid in the storage part 15 has been used up, the used storage part 15 can readily be replaced with a new one.

The heating unit 17 includes a heater 22, a heating pipe 23, a heater holder 24, a chamber sleeve 25, and others. The heating pipe 23 is a hollow pipe member (made of metal, for example), to which a liquid delivery hose 27 extending from the storage part 15 is connected, so that the aerosol-generating liquid stored in the storage part 15 can be delivered to the heating pipe 23 through the liquid delivery hose 27. The heater 22 is attached to the distal end of the heating pipe 23.

The heater 22 is a ceramic heater, for example, and provided such as to cover the outer circumference of the heating pipe 23. The heater 22 may cover part of the outer circumference of the heating pipe 23, or may cover the entire outer circumference of the heating pipe 23. The heater holder 24 is a member that holds the heater 22 and heating pipe 23, and made of a heat-resistant material such as stainless steel or heat-resistant glass, for example. When the heater 22 generates heat, the aerosol-generating liquid being delivered inside the heating pipe 23 is heated by direct heat from the inner wall of the heater 22, or by conduction of the heat of the heater 22 to the heating pipe 23. The heater 22 is not limited to the design described above and various designs may be adopted. For example, the heater 22 may be a hollow heater. One example of design in this case is that the hollow heater (heater 22) is continuously connected to a downstream end (rear end) of the heating pipe 23. The hollow heater (heater 22) is a hollow pipe member, for example, similarly to the heating pipe 23, with an internal flow path for the aerosol-generating liquid to flow through axially extending through. The hollow heater (heater 22) configured in this way can heat the aerosol-generating liquid flowing through its internal flow path as it is powered and generates heat. Thus the aerosol-generating liquid delivered from the heating pipe 23 can be heated by the hollow heater (heater 22) as the aerosol-generating liquid travels through the internal flow path of the hollow heater (heater 22).

The chamber sleeve 25 is made up of a large-diameter part 25A located on the side closer to the flavor source holding part 19, and a small-diameter part 25B located below the large-diameter part 25A, with a bottom wall 25C provided in a boundary area between the large-diameter part 25A and the small-diameter part 25B. Inside the large-diameter part 25A of the chamber sleeve 25 is formed a chamber 26 that is a space where an aerosol is generated. The small-diameter part 25B of the chamber sleeve 25 holds the heater holder 24 such that the heater holder 24 is disposed inside. The chamber 26 is formed inside the large-diameter part 25A of the chamber sleeve 25. The chamber 26 is a space where an aerosol is generated by an atomized aerosol-generating liquid. The heating pipe 23 in the heating unit 17 is disposed such as to have its distal end opening 23A facing toward inside of the chamber 26. Vapor of the aerosol-generating liquid produced as the heater 22 heats the aerosol-generating liquid inside the heating pipe 23 is introduced from the distal end opening 23A of the heating pipe 23 into the chamber 26, and an aerosol is generated by the air inside the chamber 26 and the vapor of aerosol-generating liquid mixed together. In the case where the heater 22 is a hollow heater as mentioned above and this hollow heater (heater 22) is continuously connected to the downstream end (rear end) of the heating pipe 23, the distal end of the hollow heater (heater 22) may be disposed toward inside of the chamber 26 so that the vapor of aerosol-generating liquid is introduced into the chamber 26 from the internal flow path inside the hollow heater (heater 22).

The liquid delivery unit 16 is a unit for delivering the aerosol-generating liquid stored in the storage part 15 to the heating unit 17. The liquid delivery unit 16 includes a liquid delivery hose 27 that connects the storage part 15 with the heating pipe 23 of the heating unit 17, and a liquid delivery pump 28 for delivering the aerosol-generating liquid from the storage part 15 to the heating pipe 23 through the liquid delivery hose 27. The liquid delivery pump 28 may be, for example, a piezoelectric pump, a syringe pump, a tube pump, and the like. The material used for the liquid delivery hose 27 is not limited to a particular material. For example, PTFE (polytetrafluoroethylene), silicone or the like may be used. The liquid delivery hose 27 includes a first liquid delivery hose 27A and a second liquid delivery hose 27B. The first liquid delivery hose 27A connects the storage part 15 and the liquid delivery pump 28. The second liquid delivery hose 27B connects the liquid delivery pump 28 and the heating pipe 23.

Next, the aerosol-pumping unit 21 will be described. The aerosol-pumping unit 21 includes a diaphragm pump 29 and a pneumatic transport hose 35. The diaphragm pump 29 has an air inlet 29A and an air outlet 29B. The housing 10 is provided with an air hole 103 for taking the outside air (open air) into the housing 10, so that the inside and outside of the housing 10 communicate with each other via the air hole 103. Here, there is no particular limitation on the number, size, position and the like of the air hole 103 provided to the housing 10.

One end of the pneumatic transport hose 35 is connected to the air outlet 29B of the diaphragm pump 29. The bottom wall 25C of the chamber sleeve 25 mentioned above is provided with a connection port 250. The other end of the pneumatic transport hose 35 is connected to the connection port 250, so that the air outlet 29B of the diaphragm pump 29 communicates with the chamber 26 formed inside the chamber sleeve 25 via the pneumatic transport hose 35. When the diaphragm pump 29 operates, the air brought into the housing 10 from the air hole 103 is taken into the diaphragm pump 29 from the air inlet 29A of the diaphragm pump 29, and discharged from the air outlet 29B. The air discharged from the air outlet 29B flows through the pneumatic transport hose 35 and is pumped to the chamber 26.

In the flavor dispenser apparatus 1 configured as described above, the battery 20 is connected to the processor and sound element (buzzer) mounted on the control board 14, light-emitting element 13, heater 22 of the heating unit 17, liquid delivery pump 28 of the liquid delivery unit 16, diaphragm pump 29 of the aerosol-pumping unit 21, and others via electric wiring. The processor on the control board 14 controls the power supply from the battery 20 to the light-emitting element 13, sound component 11, heater 22 of the heating unit 17, liquid delivery pump 28 of the liquid delivery unit 16, diaphragm pump 29 of the aerosol-pumping unit 21, and others to cause these various electronic components to operate in response to a device operation received from the user via the operation unit 12.

Next, examples of operating states of the flavor dispenser apparatus 1 will be illustrated. The processor on the control board 14 of the flavor dispenser apparatus 1 activates the flavor dispenser apparatus 1 when, in a power-off state, reception of an activation operation by a user via the operation unit 12 is detected. The activation operation mentioned above may be, but not limited to, an operation by the user of pressing in the operation unit 12, for example. An operation detection switch that detects an on-state and an off-state of the operation unit 12 is provided inside the housing 10, for example, so that detection by the operation detection switch of the activation operation by the user of pressing in the operation unit 12 triggers the processor on the control board 14 to output a control signal to the battery 20 for causing the various electronic components as described above to operate, whereby the flavor dispenser apparatus 1 starts to operate.

Figure 9:
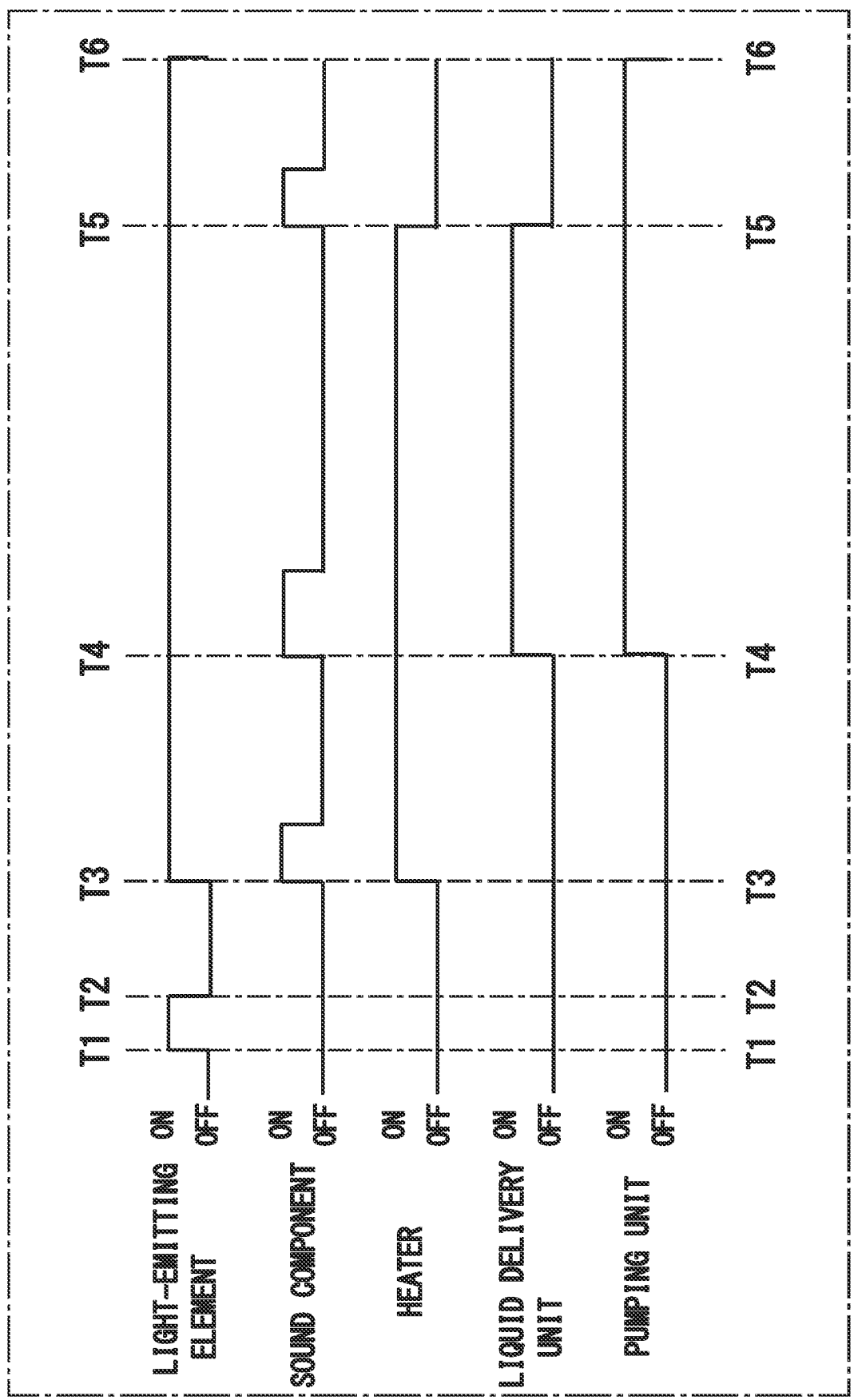
FIG. 9 is a timing chart illustrating an example of an operating state of the flavor dispenser apparatus according to Embodiment 1.

FIG. 9 is a timing chart illustrating an example of an operating state of various electronic components of the flavor dispenser apparatus 1 when in use. At time T1, when the operation detection switch detects an activation operation by the user on the operation unit 12, the processor mounted on the control board 14 may output a control signal to the battery 20 to cause the light-emitting element 13 to emit light in a first light emission mode. In the example here, the light-emitting element 13 is lit up from time T1 to time T2. The first light emission mode of the light-emitting element 13 may take any form as long as the user is notified of the activation of the flavor dispenser apparatus 1.

Next, at time T3, the processor on the control board 14 activates the heater 22 of the heating unit 17 for preliminary heating of the heating pipe 23. Specifically, the processor on the control board 14 outputs a control signal to the battery 20 to supply power from the battery 20 to the heater 22 so that the heater 22 generates heat, to heat up the heating pipe 23. The controlled temperature of the heater 22 for the preliminary heating of the heating pipe 23 may be, but not limited to, about 250 to 300° C., for example. In the example illustrated in FIG. 9, the preliminary heating of the heating pipe 23 by the heater 22 is continued from time T3 to time T4.

At time T3 when the preliminary heating of the heating pipe 23 by the heater 22 is started, the processor on the control board 14 may cause the sound component 11 to output an electronic sound in a first sound mode. The first sound mode of the sound component 11 may take any form as long as the user is notified of the start of preliminary heating of the heating pipe 23 by the heater 22. The sound component 11 need not be operated continuously until the end of preliminary heating of the heating pipe 23 by the heater 22. The processor on the control board 14 may light up the light-emitting element 13 in a second light emission mode during the period of preliminary heating (time T3 to time T4) of the heating pipe 23 by the heater 22. The second light emission mode of the light-emitting element 13 may take any form as long as the user is notified of ongoing preliminary heating of the heating pipe 23, and should preferably be different from the first light emission mode. The second light emission mode may change in the light-emitting element 13 the amount of emitted light, light emission pattern and the like stepwise or gradually toward the end of the preliminary heating period.

At the end of the preliminary heating period at time T4, the processor on the control board 14 outputs a control signal to the battery 20 to start supplying power to the liquid delivery pump 28 of the liquid delivery unit 16 and the diaphragm pump 29 of the aerosol-pumping unit 21. At this time, the heater 22 is kept powered by the battery 20.

As the liquid delivery pump 28 of the liquid delivery unit 16 starts to operate, the aerosol-generating liquid stored in the storage part 15 is delivered through the liquid delivery hose 27 to the heating pipe 23 of the heating unit 17. By then, the heating pipe 23 has already been pre-heated by the heater 22 to a high temperature, and also the heater 22 is continuously powered, so that the aerosol-generating liquid supplied through the liquid delivery hose 27 to the heating pipe 23 is successively atomized in the heating pipe 23. The aerosol-generating liquid atomized inside the heating pipe 23 then flows successively into the chamber 26 from the distal end opening 23A of the heating pipe 23.

As the diaphragm pump 29 of the aerosol-pumping unit 21 operates, the air is pumped into the chamber 26 through the pneumatic transport hose 35. Inside the chamber 26 is generated an aerosol, as the aerosol-generating liquid in the atomized state introduced from the heating pipe 23 is mixed with the air pumped from the pneumatic transport hose 35. The aerosol generated in the chamber 26 is transported toward the flavor source holding part 19 by the pressure applied by the diaphragm pump 29, i.e., the flow of compressed air pumped through the pneumatic transport hose 35. The flavor case 181 containing the flavor material 182 of the flavor cartridge 18 in this embodiment allows the aerosol to pass through the flavor case, so that the aerosol transported from the chamber 26 to the flavor source holding part 19 passes through the flavor cartridge 18, before it is delivered to the dispenser nozzle 30 that communicates with the flavor source holding part 19. The aerosol can thus be readily flavored by the flavor material 182 by passing through the flavor cartridge 18. The aerosol flavored by the flavor material 182 flows through the aerosol passage 32 of the dispenser nozzle 30, and is eventually sprayed out of (discharged from) the aerosol outlet port 31 formed at the distal end of this aerosol passage 32. In this embodiment, the chamber 26, flavor source holding part 19, and aerosol passage 32 together form an aerosol flow path.

In the example shown in FIG. 9, from time T4 to time T5, the delivery of aerosol-generating liquid by the liquid delivery unit 16, the pneumatic transport by the aerosol-pumping unit 21, and the heating by the heater 22 are controlled. Hereinafter, the period from time T4 to time T5 in which these processes are each controlled shall be referred to as "aerosol spray period". The aerosol spray period can be set to any suitable length and may be, for example, about 30 seconds.

The processor on the control board 14 may keep the heater 22 at a predetermined controlled temperature such as to exhibit hysteresis during the aerosol spray period. The controlled temperature of the heater 22 during the aerosol spray period may be, but not limited to, about 250 to 300° C., for example. The controlled temperature of the heater 22 may be set different for the aerosol spray period and for the preliminary heating period. The flavor dispenser apparatus 1 may optionally include a temperature sensor that detects the temperature of the heat generated by the heater 22, and may control the power supply to the heater 22 based on the detection results of the temperature sensor.

The amount of aerosol-generating liquid delivered by the liquid delivery pump 28 of the liquid delivery unit 16 per unit time during the aerosol spray period may be set freely. Similarly, the amount of air pumped by the diaphragm pump 29 of the aerosol-pumping unit 21 per unit time, and the degree of pressure applied by the diaphragm pump 29 during the aerosol spray period may be set freely. Namely, various settings of the liquid delivery pump 28 and diaphragm pump 29 may be set freely within a range that allows stable spraying of an intended amount of aerosol from the aerosol outlet port 31 of the dispenser nozzle 30 over the aerosol spray period.

At time T4 when the operation of spraying the aerosol is started, the processor on the control board 14 may cause the sound component 11 to output an electronic sound in a second sound mode. The second sound mode of the sound component 11 may take any form as long as the user is notified of the start of the operation of spraying the aerosol, and should preferably be different from the first sound mode in sound output pattern, length and the like. During the aerosol spray period, the processor on the control board 14 may cause the light-emitting element 13 to emit light in a third light emission mode. The third light emission mode of the light-emitting element 13 may take any form as long as the user is notified that the flavor dispenser apparatus 1 is currently spraying the aerosol, and should preferably be different from the first and second light emission modes. For example, the third light emission mode may be a mode in which the light-emitting element 13 is lit up from time T4 to time T5.

When it is time T5 at which the operation of spraying the aerosol should be ended, the processor on the control board 14 stops the operations of the heater 22 and liquid delivery pump 28. As a result, the heating unit 17 stops generation of the aerosol. Here, the period from time T5 to time T6 in FIG. 9 is referred to as "cooling interval period". In this embodiment, it is preferable to operate the diaphragm pump 29 continuously over the cooling interval period. The cooling interval period can be set freely and may be, for example, about 10 seconds. Operating the diaphragm pump 29 continuously over the cooling interval period even after the heater 22 and liquid delivery pump 28 have stopped operating allows for spraying (discharge) of the aerosol from the aerosol outlet port 31 to the outside without letting the aerosol stay behind in the chamber 26, flavor source holding part 19 (flavor cartridge 18), and aerosol passage 32.

At time T5 when the cooling interval period is started, the processor on the control board 14 may cause the sound component 11 to output an electronic sound in a third sound mode. The third sound mode of the sound component 11 may take any form as long as the user is notified of the end of aerosol generation, and should preferably be different from the first and second sound modes in sound output pattern, length and the like. During the cooling interval period, the processor on the control board 14 may cause the light-emitting element 13 to emit light in a fourth light emission mode. The fourth light emission mode of the light-emitting element 13 may take any form as long as the user is notified that the flavor dispenser apparatus 1 has ended aerosol generation and is now carrying out the operation of spraying the aerosol remaining in the aerosol passage 32 and elsewhere. The fourth light emission mode should preferably be different from the first to third light emission modes. For example, the fourth light emission mode may be a mode in which the light-emitting element 13 is gradually turned off toward time T6 when the cooling interval period ends.

Figure 10:
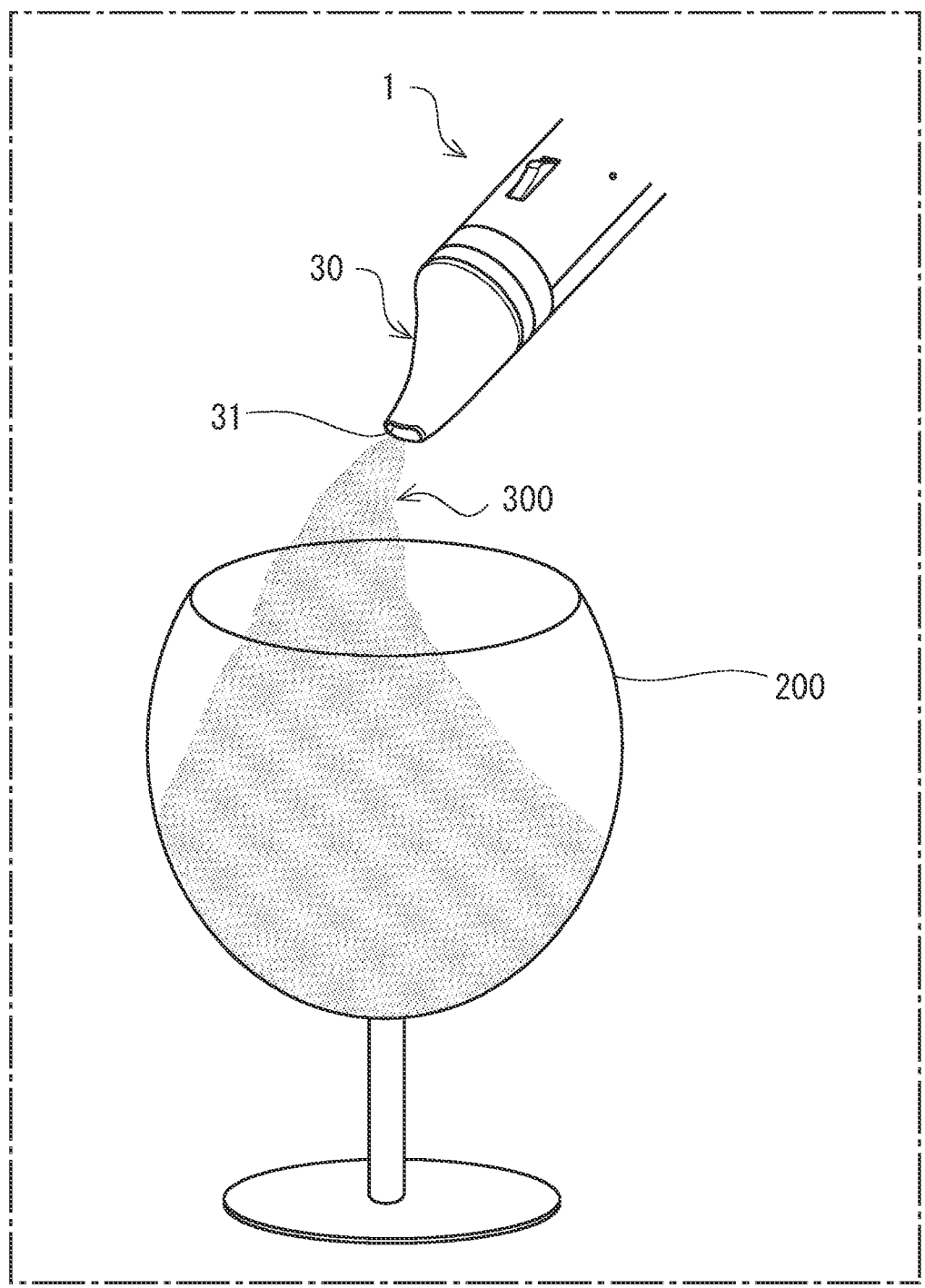
FIG. 10 is a diagram for explaining a state during use of the flavor dispenser apparatus according to Embodiment 1.

As described above, the flavor dispenser apparatus 1 in this embodiment can transport the aerosol generated in the chamber 26 of the heating unit 17 toward the flavor source holding part 19 through the chamber 26 by the aerosol-pumping unit 21 and cause the aerosol to pass through the flavor cartridge 18 (flavor source) in the flavor source holding part 19, as well as cause the aerosol flavored by the flavor material 182 in the flavor cartridge 18 to be sprayed (discharged) from the aerosol outlet port 31 of the aerosol passage 32. Since the flavor dispenser apparatus 1 in this embodiment has the hand-held housing 10 and dispenser nozzle 30, the user can readily dispense the flavored aerosol 300 sprayed (discharged) from the aerosol outlet port 31 of the dispenser nozzle 30 into dishware 200 such as a glass or a plate as shown in FIG. 10.

Figure 11:
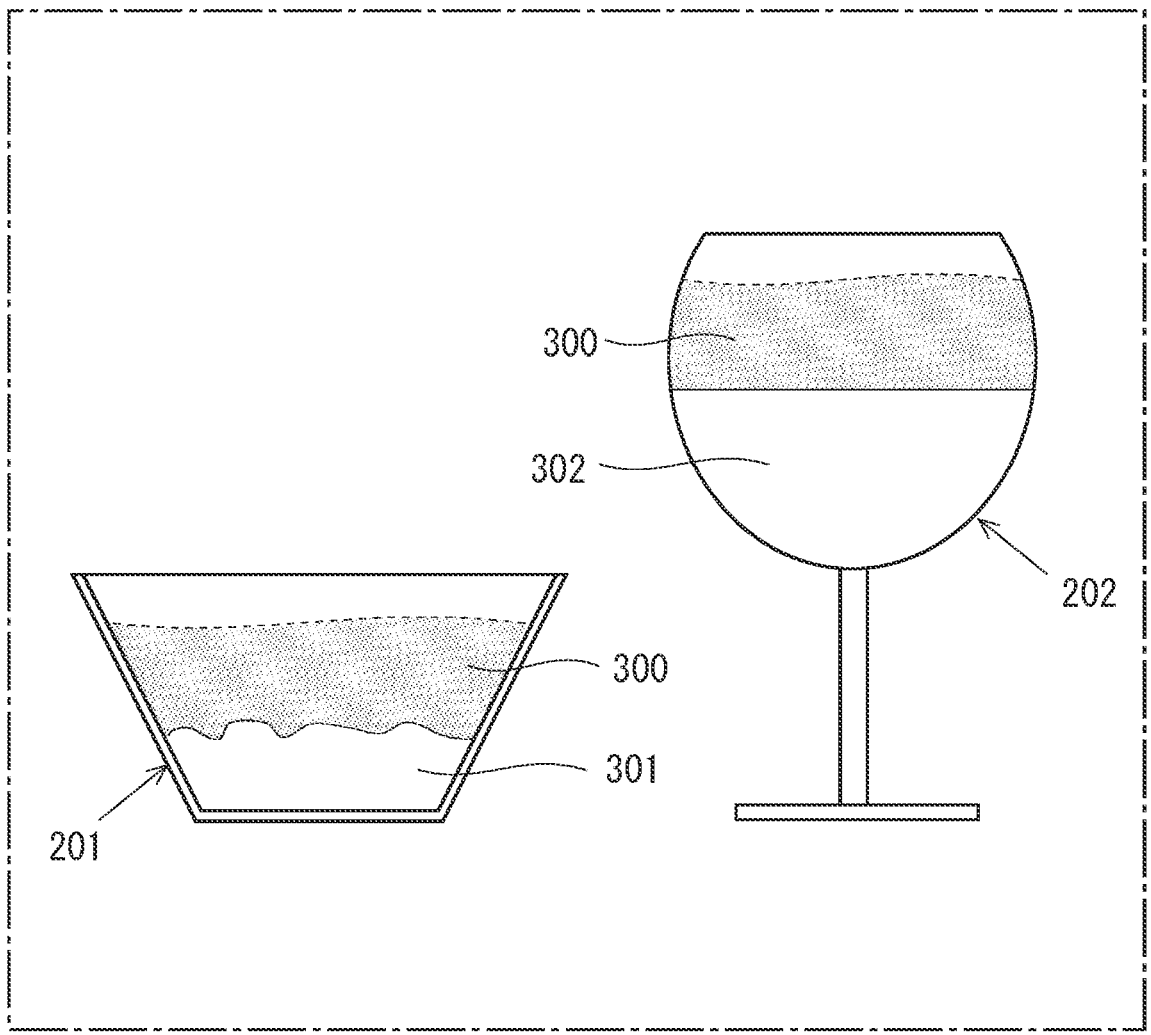
FIG. 11 is a diagram for explaining an application example of the flavor dispenser apparatus according to Embodiment 1.
Figure 12:
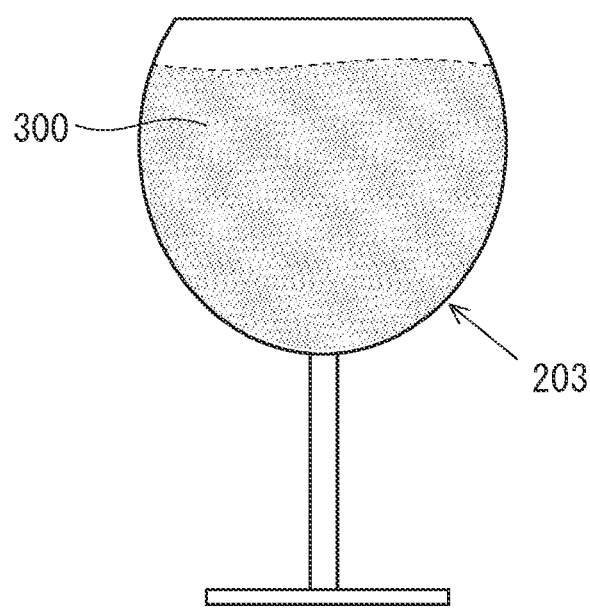
FIG. 12 is a diagram for explaining an application example of the flavor dispenser apparatus according to Embodiment 1.

FIG. 11 and FIG. 12 are diagrams illustrating an application example of the flavor dispenser apparatus 1 in which a flavored aerosol 300 has been dispensed into dishware. FIG. 11 illustrates a state in which a flavored aerosol has been dispensed into a plate 201 and a glass 202 using the flavor dispenser apparatus 1. The example here illustrates a case where a dish (food) 301 in the plate 201 or a beverage 302 in the glass 202 is added with a flavored aerosol for visual, gustatory, and olfactory enjoyment of the dish (food) 301 or beverage 302 imparted with the flavor by the flavored aerosol 300. In a restaurant or elsewhere, for example, an employee may use the flavor dispenser apparatus 1 to dispense the flavored aerosol 300 into a plate 201 or a glass 202 for customers of the restaurant to enjoy the served dish with visual, gustatory, and olfactory senses. Another example of use of the flavor dispenser apparatus 1 is to dispense a flavored aerosol 300 into an empty piece of dishware without any food or beverage or the like therein. FIG. 12 illustrates an example in which a flavored aerosol 300 has been dispensed into an empty glass 203 using the flavor dispenser apparatus 1. This way, the visual appearance or smell of the flavored aerosol 300 staying inside the glass 203 can be enjoyed.

The flavor dispenser apparatus 1 in this embodiment uses glycerin or propylene glycol and the like which is a substance having a relatively low vapor pressure as the aerosol-generating liquid so that evaporation of the atomized aerosol-generating liquid can be retarded and the flavored aerosol 300 can be made to stay inside the dishware over a long time. This prolongs the time in which the flavored aerosol dispensed into the dishware is visible so that the flavored aerosol 300 staying inside the dishware can be enjoyed over a prolonged period. Specifically, the aerosol-generating liquid should have a vapor pressure of 6.0 kPa (20° C.) or less. This makes it possible to retard evaporation of atomized aerosol-generating liquid even more favorably, so that the flavored aerosol 300 can be made to stay inside the dishware over an even longer period.

The aerosol-pumping unit 21 in this embodiment is designed to pneumatically transport the aerosol generated in the heating unit 17 from the chamber 26 toward the flavor source holding part 19 using the diaphragm pump 29, so that the aerosol can be flavored favorably in the flavor cartridge (flavor source) and the flavored aerosol 300 can be discharged favorably from the aerosol outlet port 31. The diaphragm pump 29, in particular, which is a pump that conveys the aerosol with compressed air, can provide a sufficient aerosol transport capacity without causing an excessive rise in the flow rate (flow velocity) of aerosol. This allows for quick dispensing of the flavored aerosol 300 into dishware from the aerosol outlet port 31 of the dispenser nozzle 30, while also making it harder for the flavored aerosol 300 dispensed into the dishware to diffuse to the outside. The aerosol-pumping unit 21 of this embodiment may also transport the aerosol using other means than the pressure pump. For example, the aerosol may be transported by blown air, using a blower fan or the like. The aerosol-pumping unit 21 in this embodiment may include a tank that contains a compressed gas, instead of the diaphragm pump 29, and a pump hose that pumps the compressed gas contained in the tank toward the chamber 26. The tank contains air or any gas under pressure. The tank has an outlet that discharges the compressed gas, and the compressed gas (e.g., compressed air) discharged from this outlet is pumped through the pump hose to the chamber 26. The aerosol inside the chamber 26 is conveyed toward the flavor source holding part 19 by the pressure of the compressed gas pumped to the chamber 26 from the tank in this way. Consequently, the aerosol can be flavored in the flavor cartridge 18 (flavor source), after which the flavored aerosol 300 can be discharged from the aerosol outlet port 31. In the case where such a tank is used instead of the diaphragm pump 29, the air inlet 29A and air hole 103 are not necessary.

The aerosol generated in the flavor dispenser apparatus 1 by atomizing the aerosol-generating liquid in the heating unit 17 should preferably have a particle size of about 0.1 µm to 10 µm. This can enhance the visibility of the flavored aerosol 300 dispensed into dishware in a favorable manner. The particle size of the aerosol generated in the heating unit 17 can be adjusted to a desired size through control of, for example, the composition of the aerosol-generating liquid, and parameters such as the controlled temperature of the heater 22 when generating heat, and the flow amount or flow rate (flow velocity) of the compressed air pumped by the diaphragm pump 29.

The heating unit 17 in this embodiment adopts a ceramic heater as the heater 22, so that burning of the heater 22 when powered and generating heat, or emission of an unpleasant odor resulting from such burning, can be prevented. In terms of prevention of burning during heat generation and emission of odor associated therewith, a hollow or mesh-like metal heater may also be adopted as the heater 22.

Moreover, the flavor case 181 of the flavor cartridge 18 in this embodiment is made of a transparent material as described above with reference to FIG. 5, so that the flavor material 182 contained inside is visible from the outside. Therefore, the user can easily see at a glance what type of flavor material 182 is contained inside the flavor case 181 when mounting the flavor cartridge 18 in the flavor source holding part 19 of the housing 10. This makes it unlikely that a wrong flavor cartridge 18 is set in the flavor source holding part 19 and favorably prevents the user from accidentally imparting a wrong flavor to the aerosol. The flavor case 181 may be made of a translucent material, in which case, too, the flavor material 182 is readily visible from the outside. Note, however, that the flavor case 181 need not necessarily be made of a transparent or translucent material. Since the flavor cartridge 18 can be removably mounted to the flavor source holding part 19 in this embodiment, it is no trouble to replace the flavor cartridge 18, which offers convenience in use.

Furthermore, the flavor material 182 contained in the flavor case 181 of the flavor cartridge 18 in this embodiment is in a solid form, which offers excellent ease of handling for the user. While it is difficult to use a solid-form flavor material that is insoluble to carrier such as water and propylene glycol in a common aroma diffuser, the flavor dispenser apparatus 1 of this embodiment is capable of transferring the flavor of a solid flavor material 182 to an aerosol in a favorable manner by passing the aerosol through the material.

The flavor cartridge 18 of the flavor dispenser apparatus 1 in this embodiment can be mounted in the flavor source holding part 19 in a manner visible from the outside. Specifically, a transparent window part 105 is provided to a portion of the side face 101 of the housing 10 where there is the flavor source holding part 19. Therefore, the flavor cartridge 18 mounted in the flavor source holding part 19 is visible by the user from the outside. This allows the flavor material 182 contained in the flavor case 181 of the flavor cartridge 18 mounted in the housing 10 to be recognized at a glance from the outside of the housing 10.

Figure 13:
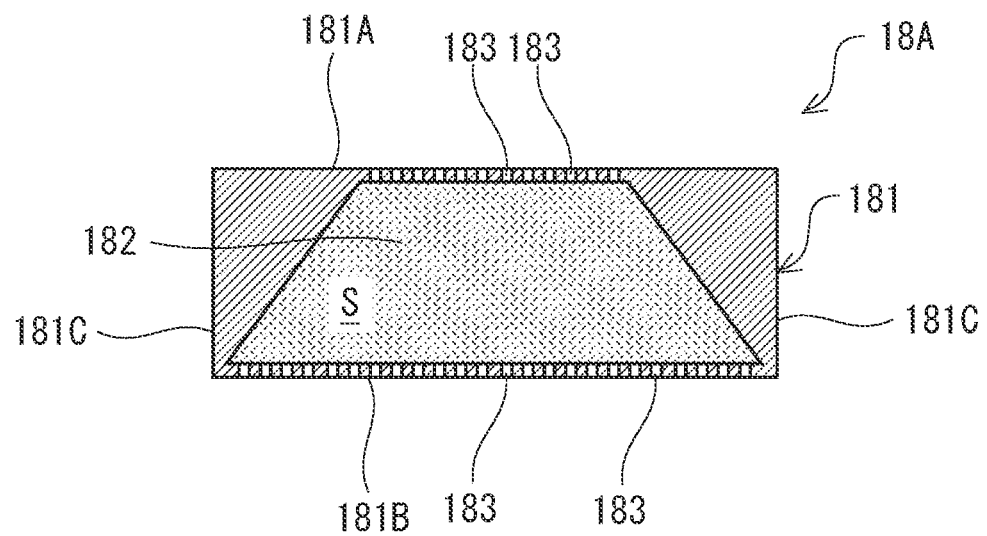
FIG. 13 is a diagram illustrating a flavor cartridge according to Variation Example 1 of Embodiment 1.

FIG. 13 is a diagram illustrating a flavor cartridge 18A according to Variation Example 1. The same reference numerals are given to the same configurations as those of the flavor cartridge 18 illustrated in FIG. 5 to omit detailed description thereof. The flavor cartridge 18A according to Variation Example 1 has a flavor case 181 that has a columnar outer shape and an accommodating space S of a truncated conical shape formed inside for the flavor material 182. The flavor case 181 of the flavor cartridge 18A gradually reduces in cross section (diameter) of the accommodating space S for the flavor material 182 from the bottom surface 181B toward the upper surface 181A. The flavor cartridge 18A in Variation Example 1 is mounted to the flavor source holding part 19 of the housing 10 such that the bottom surface 181B of the accommodating space S having a larger cross section faces the chamber 26.

Figure 14:
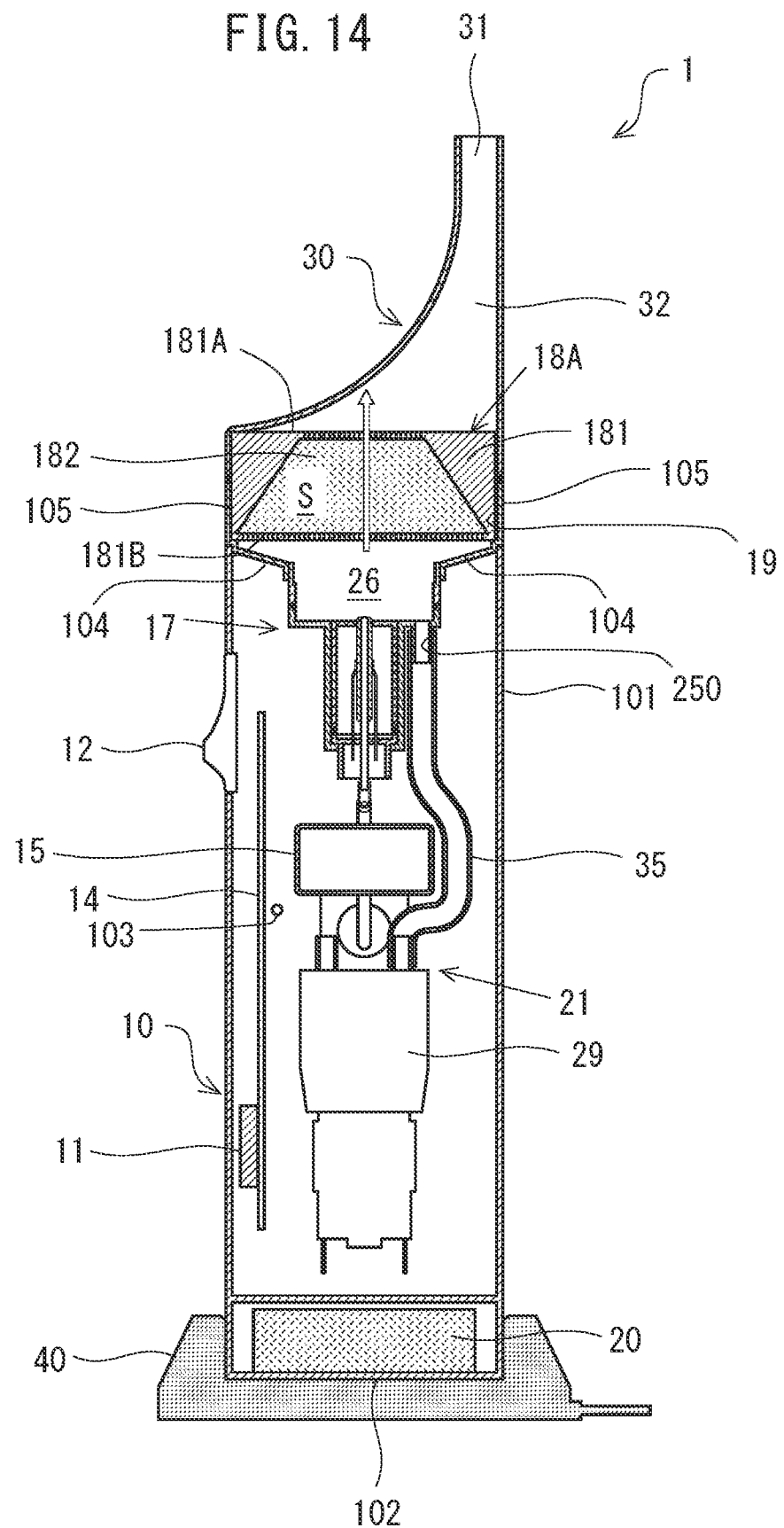
FIG. 14 is a diagram illustrating the flavor dispenser apparatus with the flavor cartridge according to Variation Example 1 of Embodiment 1 set therein.
Figure 15:
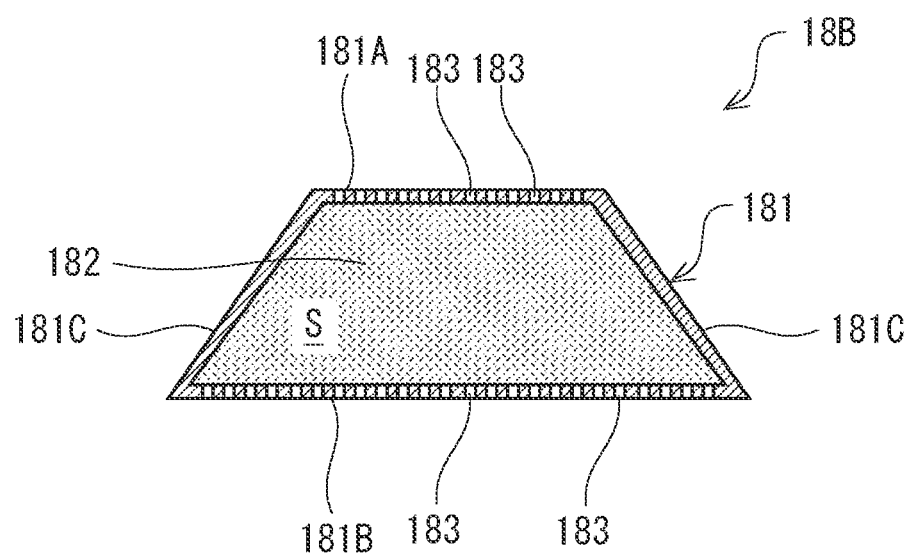
FIG. 15 is a diagram illustrating a flavor cartridge according to Variation Example 2 of Embodiment 1.

FIG. 14 is a diagram illustrating the flavor dispenser apparatus 1 with the flavor cartridge 18A according to Variation Example 1 set therein. With the flavor cartridge 18A mounted as shown in FIG. 14, the cross-sectional area of the flow path of the aerosol gradually reduces as the aerosol generated in the chamber 26 of the heating unit 17 passes through the accommodating space S of the flavor cartridge 18A. This gradual reduction in cross-sectional area of the flow path inside the flavor case 181 of the flavor cartridge 18A enables even more efficient transfer of a flavor to the aerosol from the flavor material 182 contained in the accommodating space S of the flavor case 181. That is, the flavoring of the aerosol passing through the flavor cartridge 18A can be further enhanced. Both the outside and the inner accommodating space S of the flavor case 181 may be in a truncated conical shape as in the flavor cartridge 18B according to Variation Example 2 illustrated in FIG. 15, in which case, too, similarly to the flavor cartridge 18A according to Variation Example 1, the flavoring of the passing aerosol can be achieved efficiently.

Embodiment 2

Next, a flavor dispenser apparatus 1A according to Embodiment 2 will be described. Hereinafter, the same reference numerals are given to the same configurations of the flavor dispenser apparatus 1A according to Embodiment 2 as those of the flavor dispenser apparatus 1 according to Embodiment 1 to omit detailed description thereof.

Figure 16:
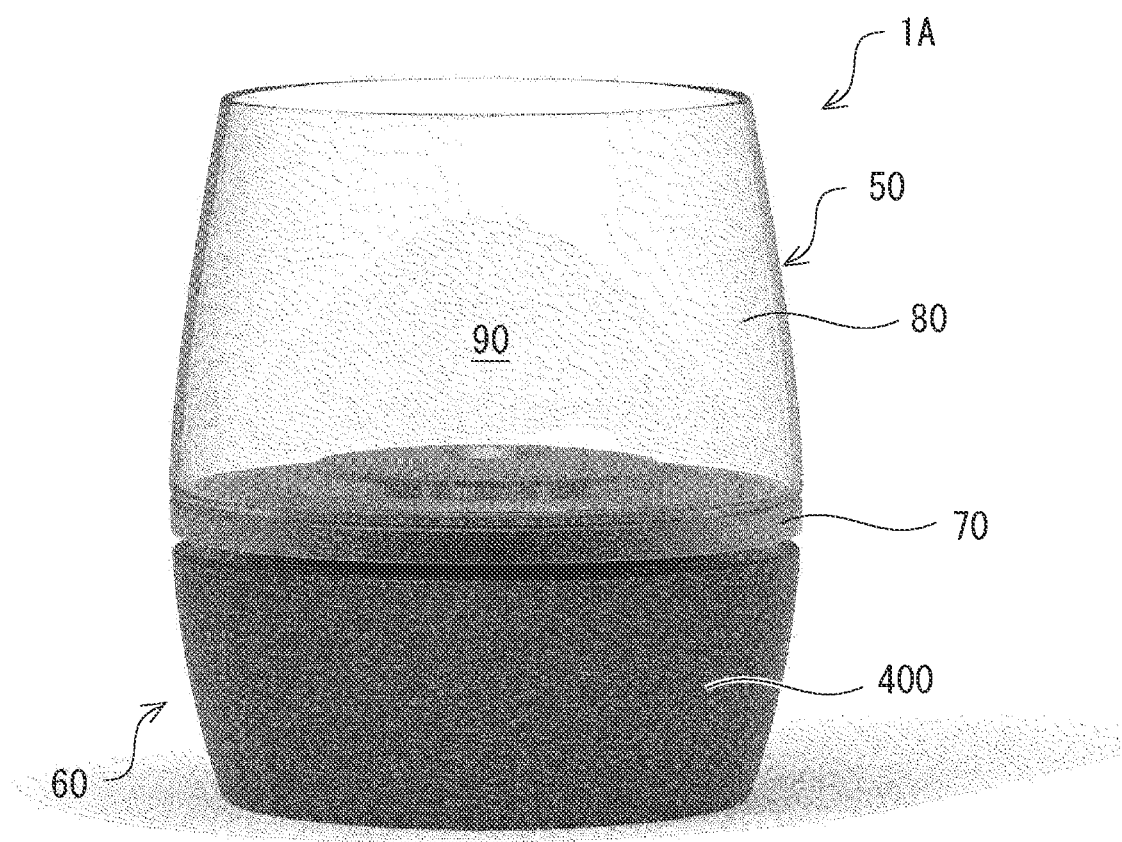
FIG. 16 is an outer view of the flavor dispenser apparatus according to Embodiment 2.

FIG. 16 is an outer view of the flavor dispenser apparatus 1A according to Embodiment 2. The flavor dispenser apparatus 1A includes an upper unit 50 and a base unit 60. The base unit 60 has a stationary base housing 400 for accommodating various components. While the flavor dispenser apparatus 1A differs from the hand-held flavor dispenser apparatus 1 in that it is a stationary device that is set on a table or the like, the basic mechanism regarding aerosol generation and flavoring has the same structure.

Figure 17:
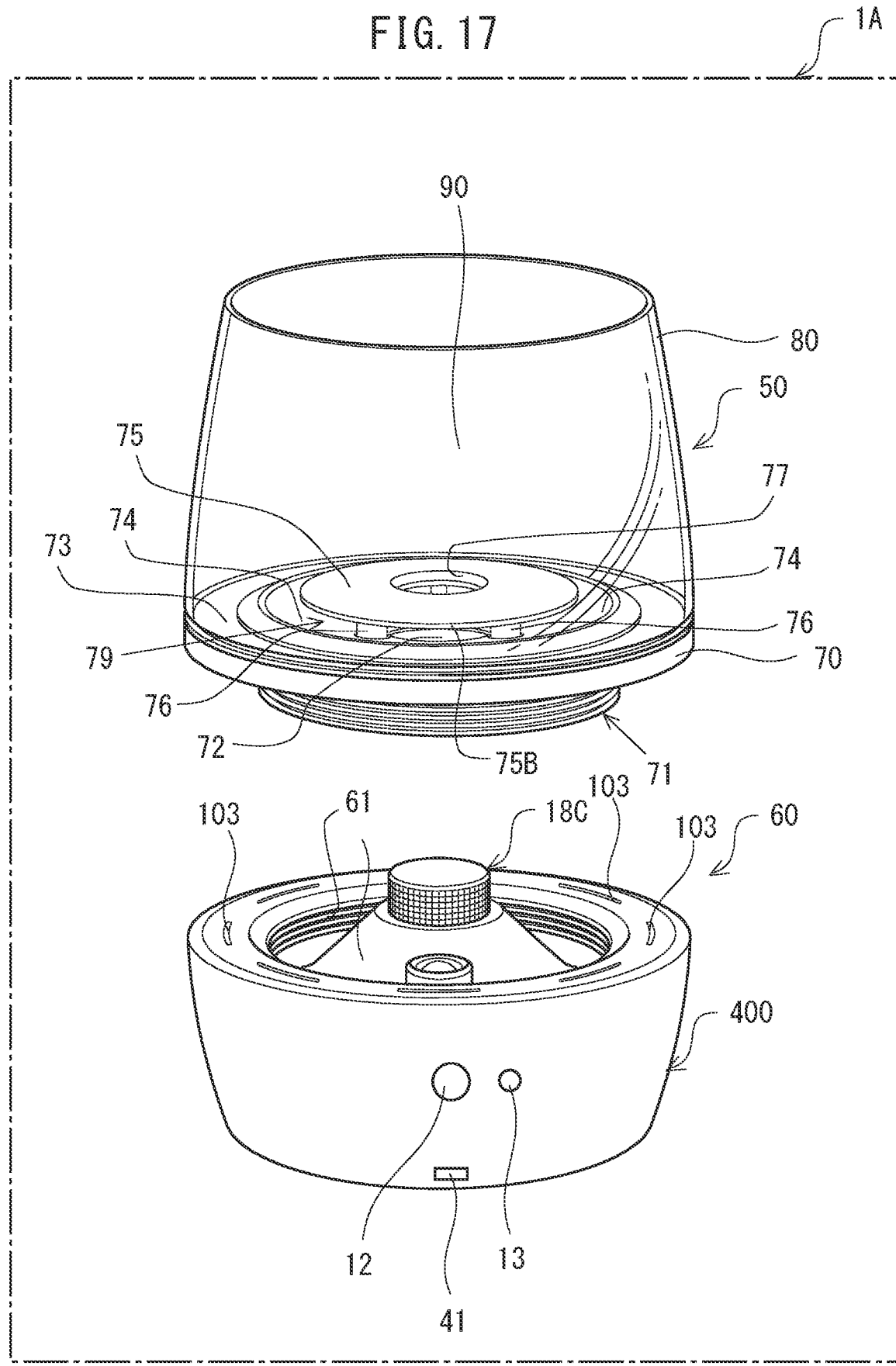
FIG. 17 is a diagram illustrating the flavor dispenser apparatus according to Embodiment 2 in which an upper unit is removed from a base unit.

The flavor dispenser apparatus 1A in this embodiment has the upper unit 50 removably attached to the base unit 60. FIG. 17 illustrates a state where the upper unit 50 is removed from the base unit 60. As shown in FIG. 16 and FIG. 17, the upper unit 50 is configured to include an aerosol discharge unit 70 and a tubular wall 80, and has a cup-like shape as a whole. Inside the upper unit 50 is formed an aerosol storage part 90 that is a space for storing a flavored aerosol flavored by a flavor source. Herein, for convenience of explanation, one side of the aerosol discharge unit 70 facing the aerosol storage part 90 shall be referred to as upper surface, and the opposite side as lower surface.

The tubular wall 80 of the upper unit 50 is a tubular member made of a transparent resin or glass, for example, and divides the aerosol storage part 90 from the lateral ambient space. In the example illustrated in FIG. 16 and FIG. 17, the aerosol discharge unit 70 is circular in plan view. The tubular wall 80 is cylindrical and stands upright from an outer peripheral portion of the aerosol discharge unit 70.

As shown in FIG. 17, in a lower part of the aerosol discharge unit 70 is provided an upper unit-side connecting portion 71 for connecting the upper unit 50 removably to the base unit 60. On the other hand, the base unit 60 has a base unit-side connecting portion 61 removably attachable to the upper unit-side connecting portion 71. The base unit-side connecting portion 61 and the upper unit-side connecting portion 71 can make screw engagement, for example, and can disengage from each other, which enables freely removable attachment of the upper unit 50 to the base unit 60. In this embodiment, the aerosol discharge unit 70 of the upper unit 50 and the base housing 400 constitute the housing 10A of the flavor dispenser apparatus 1. The base unit 60 is provided with the operation unit 12, light-emitting element 13, power supply port 41, and so on. The operation unit 12 may be, for example, but not limited to, a push button to be operated by the user. A terminal of a power cable can be connected to the power supply port 41.

Figure 18:
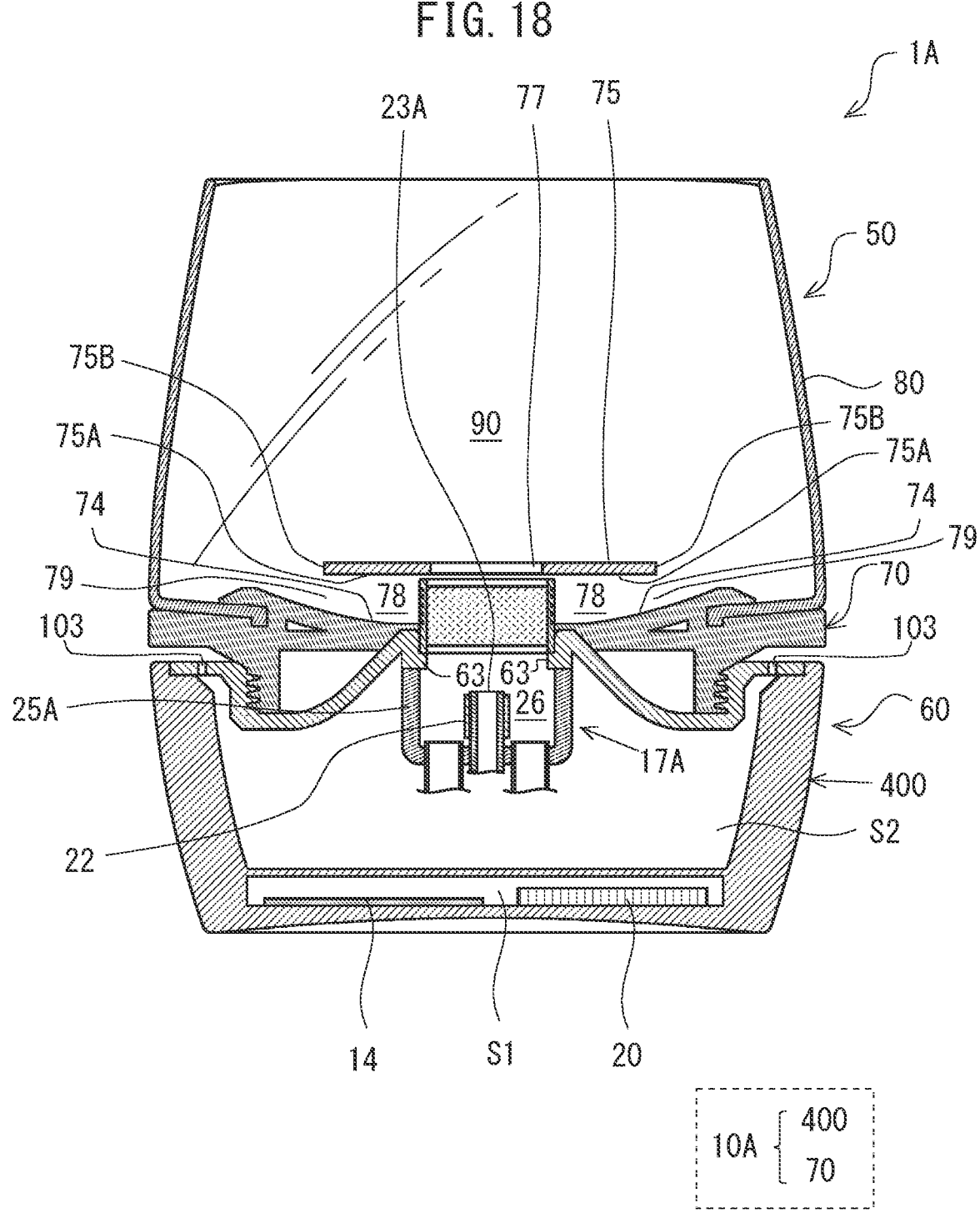
FIG. 18 is a diagram illustrating a longitudinal cross section of the flavor dispenser apparatus according to Embodiment 2.
Figure 19:
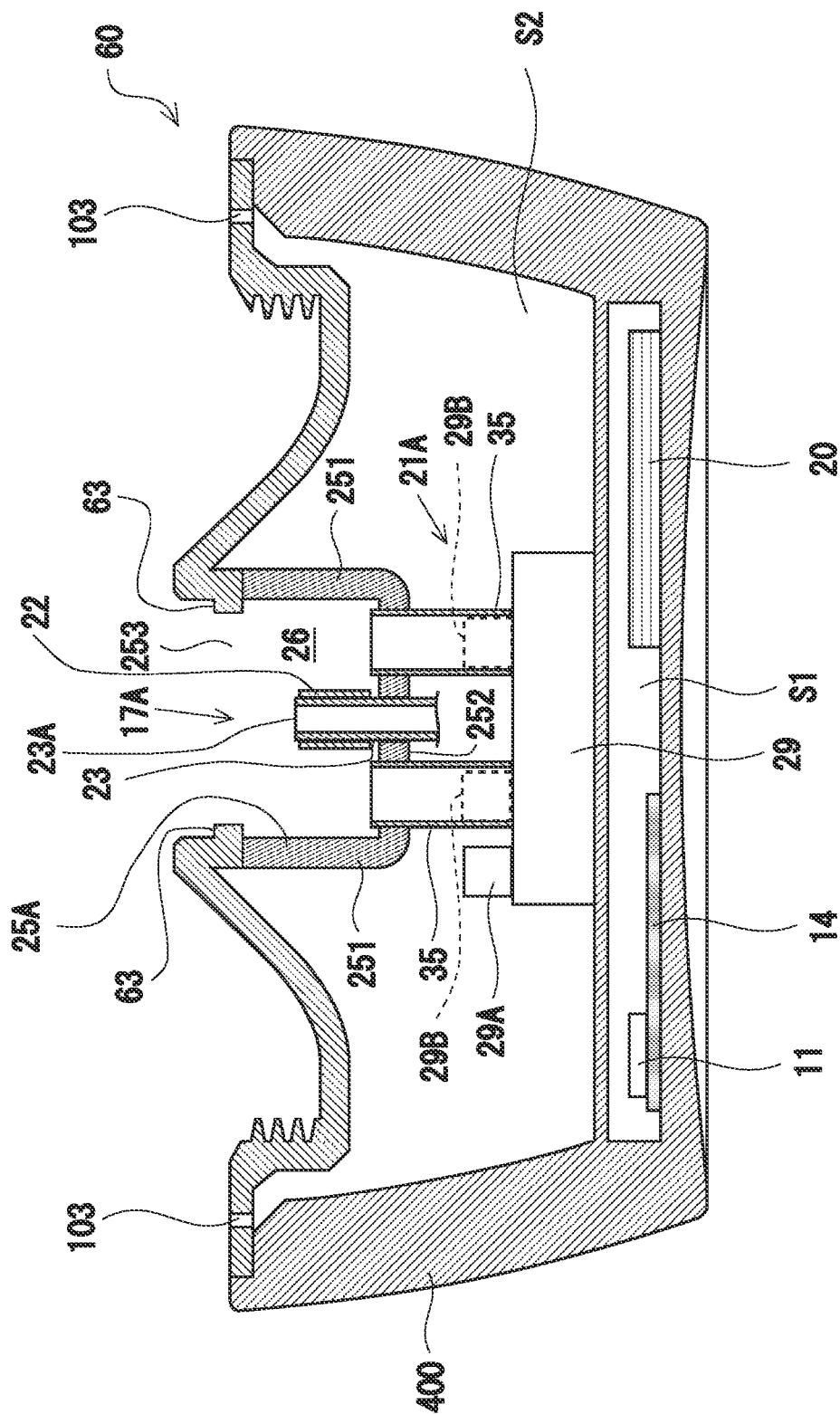
FIG. 19 is a diagram illustrating an internal structure of the base unit of the flavor dispenser apparatus according to Embodiment 2.
Figure 20:
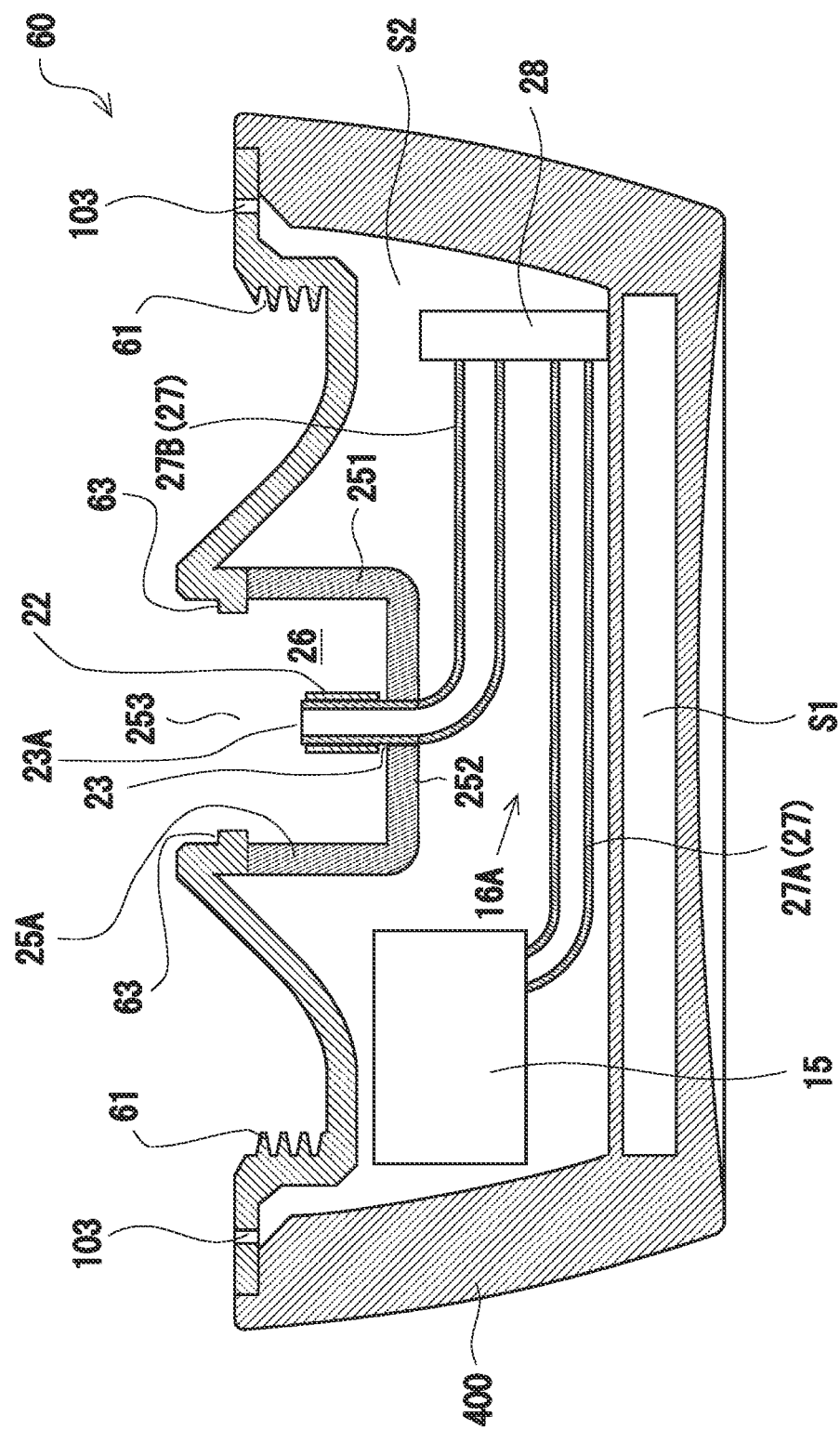
FIG. 20 is a diagram illustrating the internal structure of the base unit of the flavor dispenser apparatus according to Embodiment 2.

FIG. 18 is a diagram illustrating a longitudinal cross section of the flavor dispenser apparatus 1A according to Embodiment 2. FIG. 19 and FIG. 20 are diagrams illustrating an internal structure of the base unit 60 (base housing 400). FIG. 19 and FIG. 20 illustrate a longitudinal cross section of the base unit 60 (base housing 400) viewed from directions at 90° to each other. Inside the base housing 400 of the base unit 60 are formed a first accommodating space S1 and a second accommodating space S2, from the bottom side up. As shown in FIG. 19, the control board 14 and battery 20 are disposed inside the first accommodating space S1 of the base unit 60 (base housing 400). The battery 20 can be charged by power supplied from a power cable connected to the power supply port 41 of the base unit 60, for example. Alternatively, the battery 20 may be charged by power supplied from a wireless power supply system, for example.

The second accommodating space S2 of the base unit 60 (base housing 400) accommodates the storage part 15, liquid delivery unit 16A, heating unit 17A, aerosol-pumping unit 21A, and so on. The heating unit 17A includes a heater 22, a heating pipe 23, a chamber sleeve 25D, and others. The chamber sleeve 25D is a tubular member with a bottom, having a side wall 251 and a bottom wall 252, and forming the chamber 26 inside. In a central portion of the bottom wall 252 of the chamber sleeve 25D is formed an insertion hole for the heating pipe 23 to pass through, and the heating pipe 23 is fixed to the chamber sleeve 25D so that the heating pipe 23 is positioned inside the chamber 26. The heater 22 is provided such as to cover the outer circumference of the heating pipe 23.

Similarly to Embodiment 1, the liquid delivery unit 16A includes a liquid delivery hose 27 (first liquid delivery hose 27A and second liquid delivery hose 27B), and a liquid delivery pump 28. The first liquid delivery hose 27A of the liquid delivery unit 16 connects the storage part 15 and the liquid delivery pump 28. The second liquid delivery hose 27B connects the liquid delivery pump 28 and the heating pipe 23. The aerosol-pumping unit 21A includes a diaphragm pump 29 and a pair of pneumatic transport hoses 35. The diaphragm pump 29 has an air inlet 29A and a pair of air outlets 29B. The housing 10A is provided with air holes 103 for taking the outside air (open air) into the housing 10A, so that the inside and outside of the housing 10 communicate with each other via the air holes 103. The bottom wall 252 of the chamber sleeve 25D is formed with insertion holes for the pair of pneumatic transport hoses 35 to pass through, and an end portion of each pneumatic transport hose 35 is fixed to the chamber sleeve 25D so that the pair of pneumatic transport hoses 35 face the inside of the chamber 26.

Figure 21:
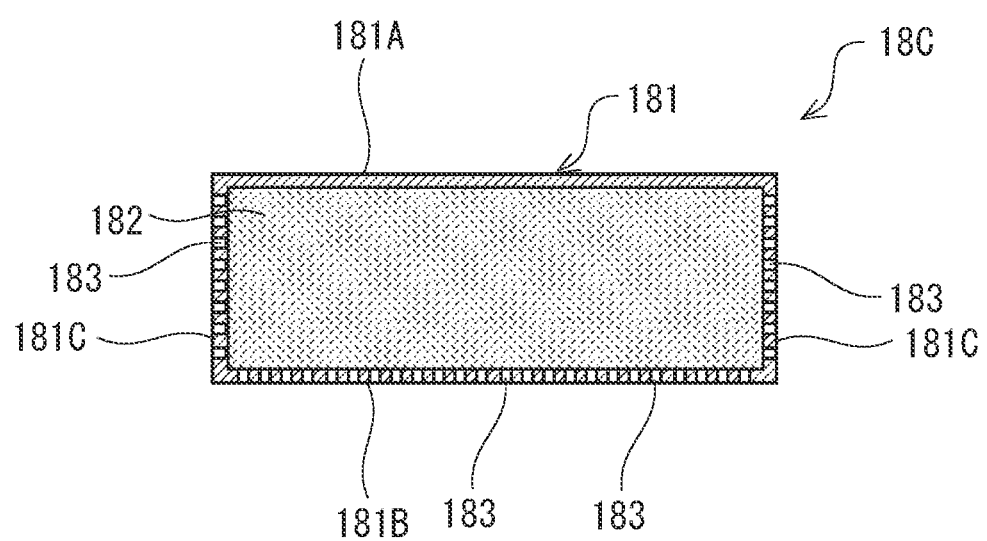
FIG. 21 is a diagram illustrating one example of the flavor cartridge used in the flavor dispenser apparatus according to Embodiment 2.
Figure 22:
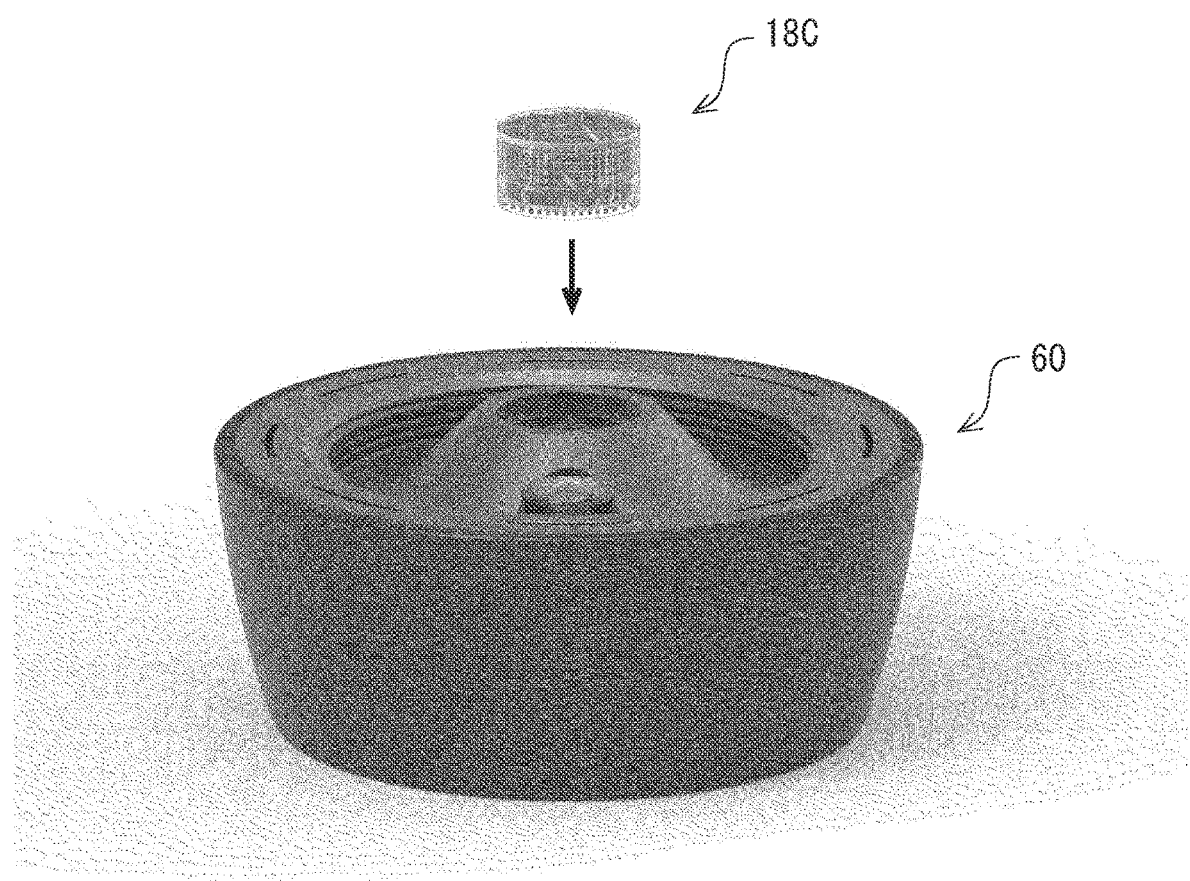
FIG. 22 is a diagram for explaining a method of mounting a flavor cartridge to a flavor source holding part of the flavor dispenser apparatus according to Embodiment 2.

Further, a flavor source holding part 63 that supports the flavor cartridge 18C is provided in an upper part of the opening 253 of the chamber sleeve 25D of the base unit 60. FIG. 21 is a diagram illustrating one example of the flavor cartridge 18C used in the flavor dispenser apparatus 1A according to Embodiment 2. The flavor cartridge 18C has a flavor case 181 containing a solid flavor material 182 and formed with air holes 183 in the bottom surface 181B and side faces 181C for letting the aerosol pass through. Namely, the flavor case 181 of the flavor cartridge 18C can take in the aerosol through the bottom surface 181B, and let the aerosol out through the side faces 181C after the flavor has been imparted by the flavor material 182. The flavor case 181 of the flavor cartridge 18C is made of a transparent or translucent material similarly to the flavor cases described in the foregoing. FIG. 18 shows a state in which the flavor cartridge 18C is mounted in the flavor source holding part 63 such that the flavor source holding part 63 supports the bottom surface 181B of the flavor case 181. The flavor cartridge 18C can be mounted to the flavor source holding part 63 easily by lowering the flavor cartridge 18C down from above the base unit 60 and placing it onto the flavor source holding part 63 illustrated in FIG. 22.

Next, the detail of the upper unit 50 of the flavor dispenser apparatus 1A will be described. In a central portion of the aerosol discharge unit 70 of the upper unit 50 is formed a cartridge insertion hole 72 (see FIG. 17). The cartridge insertion hole 72 of the aerosol discharge unit 70 is a through hole for the flavor cartridge 18C mounted in the flavor source holding part 63 of the base unit 60 to go into, when the upper unit 50 is attached to the base unit 60. When the upper unit 50 is attached to the base unit 60, the flavor cartridge 18C received in the cartridge insertion hole 72 faces toward the inside of the aerosol storage part 90 of the upper unit 50 as shown in FIG. 18.

Figure 23:
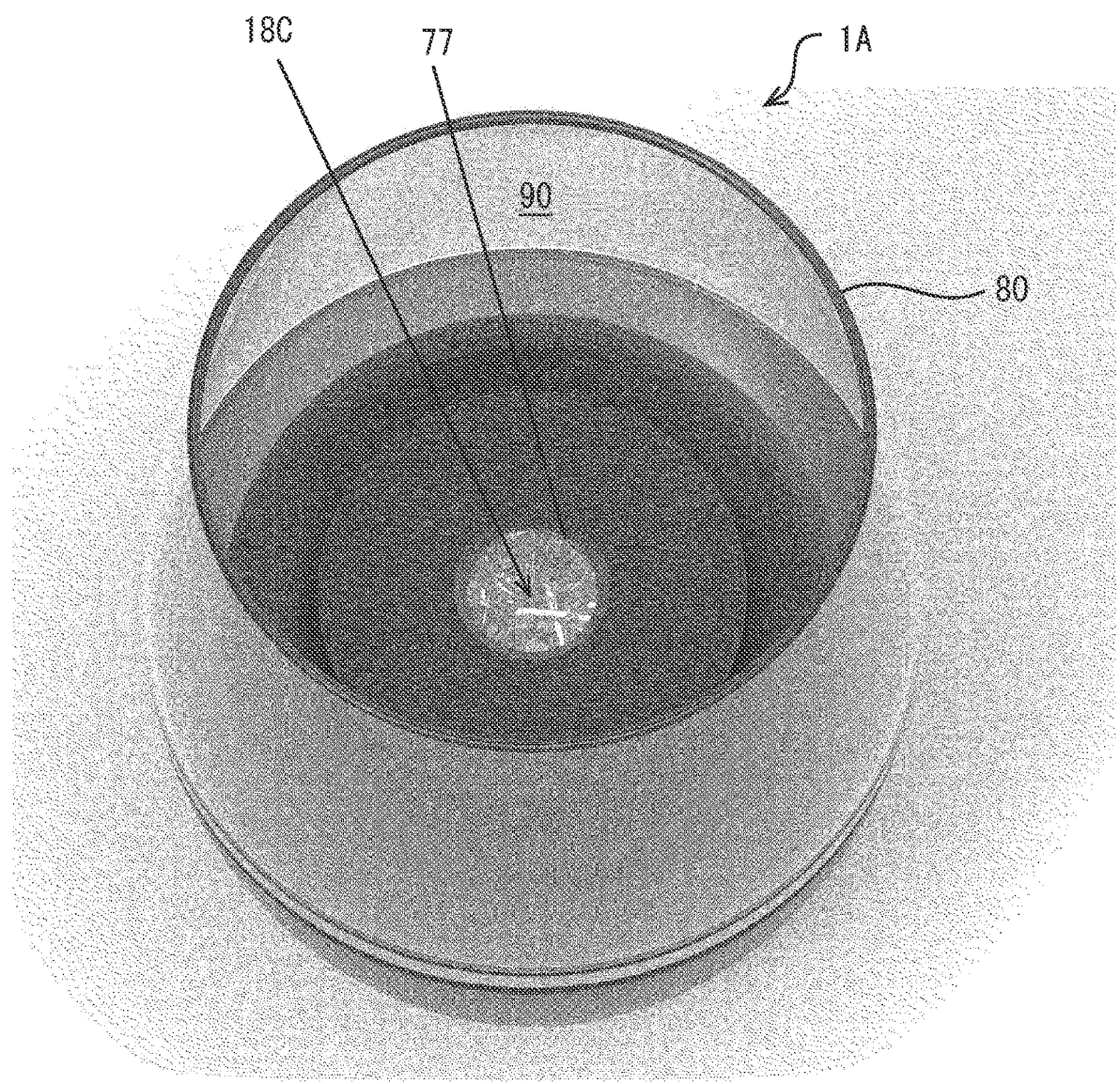
FIG. 23 is a diagram of the flavor dispenser apparatus according to Embodiment 2 viewed diagonally from above.

As shown in FIG. 17 and FIG. 18, the upper surface 73 of the aerosol discharge unit 70 is provided with a concave portion 74 dented in a crater or bowl shape around the cartridge insertion hole 72. Above the concave portion 74 of the aerosol discharge unit 70 is a laterally extending guide wall 75 for covering the upper side of the flavor cartridge 18C. In the example shown in FIG. 17, the guide wall 75 has a disc shape, and is supported by support pieces 76 standing upright from the concave portion 74 of the aerosol discharge unit 70. A circular open window 77 extending through the guide wall 75 is formed in a central portion of the guide wall 75. Therefore, as illustrated in FIG. 23, the flavor cartridge 18C mounted in the flavor source holding part 63 of the base unit 60 is visible from above.

A guide surface 75A opposite the concave portion 74 is formed on the underside of the guide wall 75. As shown in FIG. 18, the guide wall 75 is provided such that the guide surface 75A is positioned slightly higher than the position of the upper surface 181A of the flavor cartridge 18C mounted in the flavor source holding part 63 so that the guide wall 75 does not interfere with the upper surface 181A. In an area between the concave portion 74 and the guide wall 75 of the aerosol discharge unit 70 is formed an aerosol passage 78 for the aerosol to flow, and the aerosol outlet port 79 is formed below an outer peripheral edge 75B of the guide wall 75. In the flavor dispenser apparatus 1A configured as described above, the flavor cartridge 18C is positioned in the aerosol passage 78. The aerosol outlet port 79 is positioned in an upper part of the housing 10A.

Next, the operation of the flavor dispenser apparatus 1A according to Embodiment 2 will be described. The processor on the control board 14 activates the flavor dispenser apparatus 1 when an activation operation by a user via the operation unit 12 of the flavor dispenser apparatus 1A is received. The processor on the control board 14 of the flavor dispenser apparatus 1A controls the liquid delivery unit 16A, heating unit 17A, aerosol-pumping unit 21A and others in accordance with the timing chart described with reference to FIG. 9, for example.

Namely, the processor on the control board 14 activates the heater 22 of the heating unit 17A for preliminary heating of the heating pipe 23. After completion of preliminary heating of the heating pipe 23 by the heater 22, the processor on the control board 14 controls the delivery of the aerosol-generating liquid by the liquid delivery unit 16A and the pneumatic transport by the aerosol-pumping unit 21A, while continuously controlling the heating by the heater 22. As the liquid delivery pump 28 of the liquid delivery unit 16A starts to operate, the aerosol-generating liquid stored in the storage part 15 is delivered through the liquid delivery hose 27 (first liquid delivery hose 27A and second liquid delivery hose 27B) to the heating pipe 23 of the heating unit 17A. The aerosol-generating liquid delivered to the heating pipe 23 is heated by the hot heating pipe 23 and atomized, and the atomized aerosol-generating liquid inside the heating pipe 23 flows into the chamber 26 from the distal end opening 23A of the heating pipe 23.

The diaphragm pump 29 of the aerosol-pumping unit 21A operates to take in the air introduced from the air holes 103 into the base housing 400 into the diaphragm pump 29 from the air inlet 29A of the diaphragm pump 29, and to discharge the air from the pair of air outlets 29B. This results in the air pumped into the chamber 26 through the pair of pneumatic transport hoses 35. As a result, an aerosol is generated in the chamber 26, and this aerosol is pushed out of the chamber 26 toward the flavor cartridge 18C. The aerosol pumped from the chamber 26 to the flavor cartridge 18C under pressure is taken into the flavor cartridge 18C (flavor case 181) through the bottom surface 181B, and discharged through the side faces 181C. The aerosol is flavored by the flavor material 182 contained in the flavor case 181 in the process of traveling through the flavor cartridge 18C this way. The flavored aerosol after passing through the flavor cartridge 18C flows through the aerosol passage 78, and is sprayed (discharged) from the aerosol outlet port 79 located at the distal end of the aerosol passage 78 into the aerosol storage part 90.

Since the flavor dispenser apparatus 1A in this embodiment has the tubular wall 80 of the upper unit 50 lateral to the aerosol storage part 90, the flavored aerosol sprayed (discharged) from the aerosol outlet port 79 can be made to stay in the aerosol storage part 90 over a long time. The flavor dispenser apparatus 1A may for example be used by individuals at home. During a meal or the like, for example, the flavor dispenser apparatus 1A may be set on a table, and, using the flavor dispenser apparatus 1, one can enjoy watching the flavored aerosol staying inside the aerosol storage part 90 and enjoy the smell. Alternatively, the flavor dispenser apparatus 1A may be operated with some food put inside the aerosol storage part 90, to impart a flavor to the food in the aerosol storage part 90 with the flavored aerosol.

In the flavor dispenser apparatus 1A of this embodiment, the guide wall 75 is extended sideways (toward the tubular wall 80) at the bottom of the aerosol storage part 90, and this guide wall 75 covers the upper side of the flavor cartridge 18C, so that the flavored aerosol can be sprayed (discharged) sideways (toward the tubular wall 80) from the aerosol outlet port 79. This way, the flavored aerosol is less likely to flow out of the aerosol storage part 90 from the upper open end of the tubular wall 80, and thus the flavored aerosol can be made to stay in the aerosol storage part 90 over an even longer time.

Embodiment 3

Next, a flavor dispenser apparatus 1B according to Embodiment 3 will be described. The flavor dispenser apparatus 1B according to Embodiment 3 has substantially the same structure as that of the flavor dispenser apparatus 1 according to Embodiment 1 except for the shape of the chamber 26 and the connection design of the pneumatic transport hose 35 to the chamber 26 that differ from those of the flavor dispenser apparatus 1 of Embodiment 1. Hereinafter, the difference between the flavor dispenser apparatus 1B according to Embodiment 3 and the flavor dispenser apparatus 1 according to Embodiment 1 will mainly be described. The same reference numerals are given to the same configurations as those of the flavor dispenser apparatus 1 according to Embodiment 1 to omit detailed description thereof.

Figure 24:
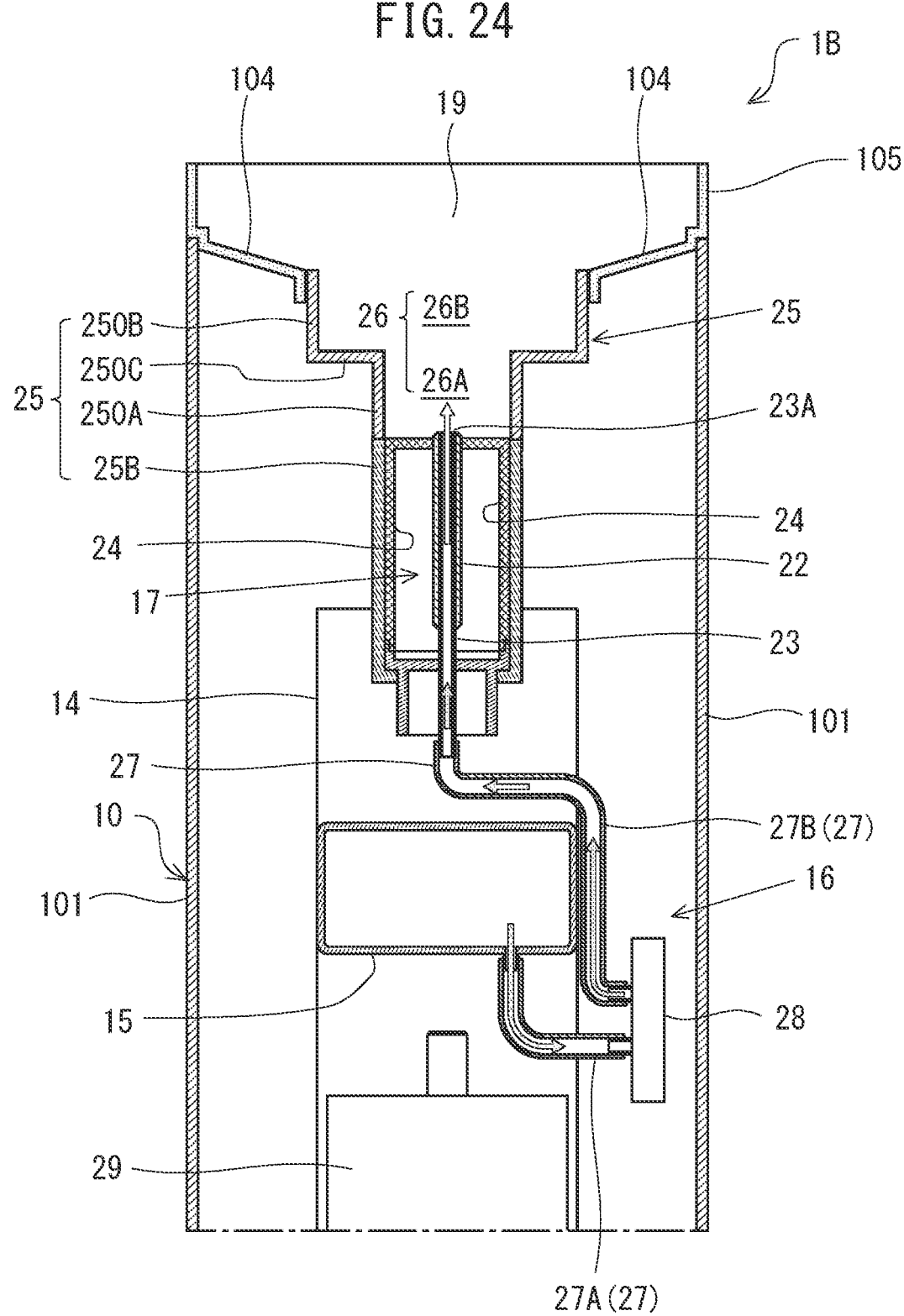
FIG. 24 is a diagram for explaining the details of a storage part, a liquid delivery unit, a heating unit, and an aerosol-pumping unit according to Embodiment 3.
Figure 25:
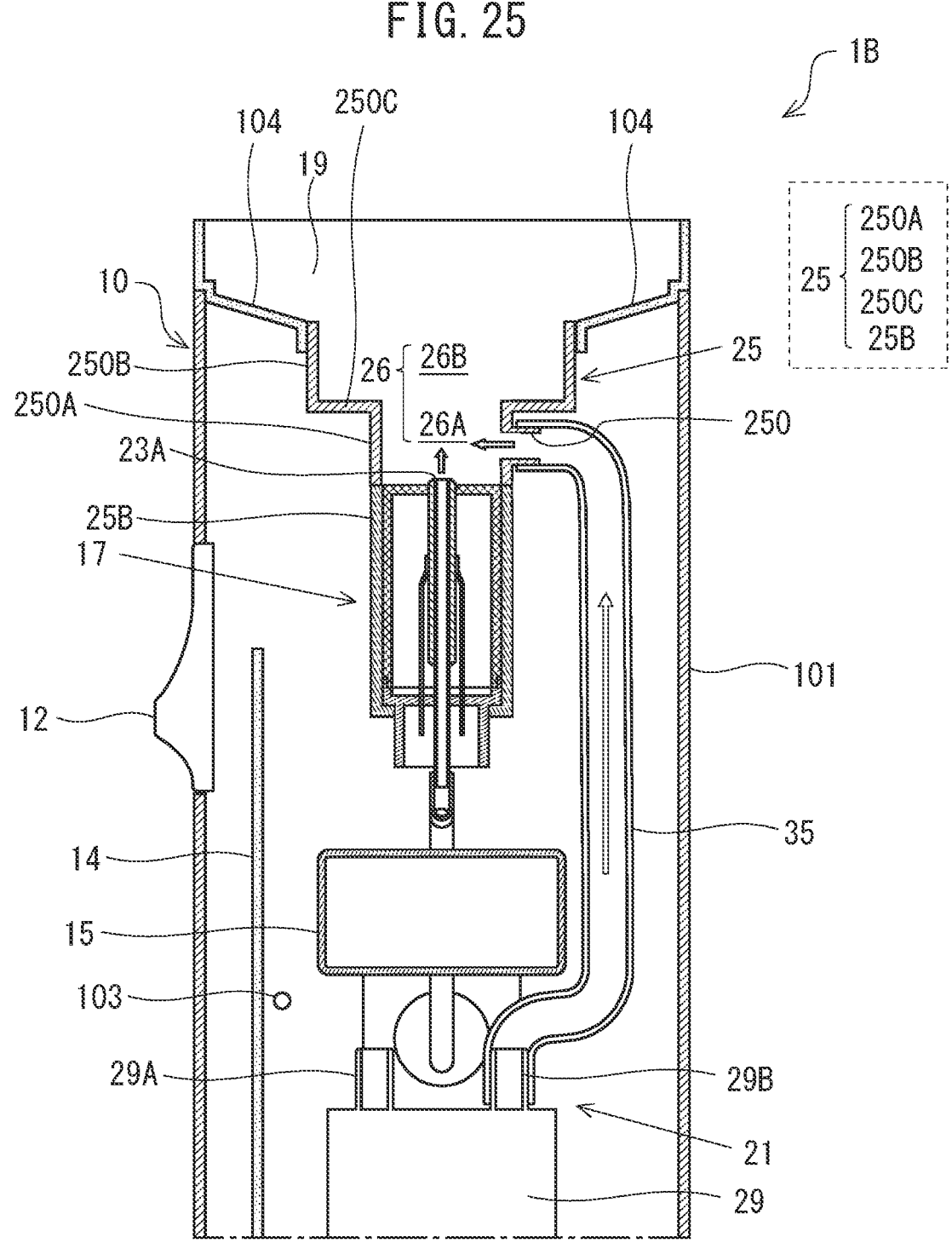
FIG. 25 is a diagram for explaining the details of the storage part, liquid delivery unit, heating unit, and aerosol-pumping unit according to Embodiment 3.

FIG. 24 and FIG. 25 are diagrams for explaining the details of the storage unit 15, liquid delivery unit 16, heating unit 17, and aerosol-pumping unit 21 of the flavor dispenser apparatus 1B according to Embodiment 3. FIG. 24 and FIG. 25 illustrate part of the internal structure along longitudinal cross sections that are perpendicular to each other of the flavor dispenser apparatus 1B.

The chamber sleeve 25 in the flavor dispenser apparatus 1B according to Embodiment 3 includes a first tubular wall portion 250A extending upward from the small-diameter part 25B, a second tubular wall portion 250B having a larger diameter than the first tubular wall portion 250A and continuously extending upward from the first tubular wall portion 250A, and a connecting wall portion 250C connecting an upper end portion of the first tubular wall portion 250A and a lower end portion of the second tubular wall portion 250B. The small-diameter part 25B in this embodiment has the same structure as that of the small-diameter part 25B of Embodiment 1 and holds the heater holder 24 inside. In this embodiment, the first tubular wall portion 250A and second tubular wall portion 250B are both cylindrical sleeve members coaxial to each other. The chamber 26 is formed inside the first tubular wall portion 250A and second tubular wall portion 250B. In the example shown in FIG. 24 and FIG. 25, the first tubular wall portion 250A has the same diameter as the small-diameter part 25B. Note, the first tubular wall portion 250A may have a larger diameter than that of the small-diameter part 25B.

In the example shown in FIG. 24 and FIG. 25, the connecting wall portion 250C formed in a boundary area between the first tubular wall portion 250A and the second tubular wall portion 250B extends in a direction perpendicular to the axial direction of the first tubular wall portion 250A and second tubular wall portion 250B, but the connecting wall portion 250C may be inclined to this axial direction. The chamber 26 in this embodiment is configured to include a first chamber part 26A formed inside the first tubular wall portion 250A and a second chamber part 26B formed inside the second tubular wall portion 250B. As is clear from FIG. 24 and FIG. 25, the second chamber part 26B has a larger cross section than the first chamber part 26A. More particularly, the first chamber part 26A and second chamber part 26B are formed as coaxial columnar cavities, the second chamber part 26B being larger in diameter compared to the first chamber part 26A. The second chamber part 26B is located above the first chamber part 26A, and disposed to face the flavor source holding part 19 that holds the flavor cartridge 18.

As shown in FIG. 25, a connection port 250 is provided to the first tubular wall portion 250A, and the pneumatic transport hose 35 is connected to the connection port 250. In other words, one end of the pneumatic transport hose 35 communicates with the first chamber part 26A via the connection port 250 of the first tubular wall portion 250A.

As shown in FIG. 25, the pneumatic transport hose 35 is connected from a lateral direction to the connection port 250 of the first tubular wall portion 250A, which is different in connection design from the flavor dispenser apparatus 1 according to Embodiment 1 in which the pneumatic transport hose 35 is connected to the chamber 26 from the underside.

In the flavor dispenser apparatus 1B configured as described above, when the diaphragm pump 29 is operated, the air flowing through the pneumatic transport hose 35 flows (laterally) into the first chamber part 26A from a lateral direction toward the radial center of the first chamber part 26A. On the other hand, as shown in FIG. 24 and FIG. 25, the heating pipe 23 in the heating unit 17 extends along the axial direction of the first chamber part 26A, with its distal end opening 23A facing toward inside of the first chamber part 26A at the bottom in the center of the first chamber part 26A. Therefore, during the operation of the liquid delivery unit 16 and heating unit 17, when the aerosol-generating liquid is delivered through the liquid delivery hose 27 to the heating pipe 23 of the heating unit 17, and when the aerosol-generating liquid inside the heating pipe 23 is heated by the heater 22, the vapor of the aerosol-generating liquid thus formed is discharged through the distal end opening 23A of the heating pipe 23 from the underside (bottom) into the first chamber 26A upward along the axial direction of the first chamber 26A.

As described above, the flavor dispenser apparatus 1B is designed such that the discharging direction of the vapor of the aerosol-generating liquid expelled from the heating pipe 23 of the heating unit 17 into the first chamber part 26A is perpendicular to the flowing direction of air pumped into the first chamber part 26A through the pneumatic transport hose 35 of the aerosol-pumping unit 21. This further advances the mixing of the vaporized (atomized) aerosol-generating liquid introduced from the heating pipe 23 and the air pumped from the pneumatic transport hose 35 in the first chamber part 26A, which increases and makes uniform the concentration of aerosol generated inside the first chamber part 26A.

Moreover, the chamber 26 of this embodiment has a structure in which the second chamber part 26B with a larger diameter facing the flavor source holding part 19 that holds the flavor cartridge 18 is stacked upon the first chamber part 26A with a small diameter. Therefore, the aerosol, which is produced by the mixing of the vaporized (atomized) aerosol-generating liquid introduced from the heating pipe 23 and the air from the pneumatic transport hose 35 in the first chamber part 26A, is successively pushed from the first chamber part 26A with a small diameter to the second chamber part 26B with a large diameter, before passing through the flavor cartridge 18 held in the flavor source holding part 19 and thereby being flavored. The aerosol being pushed herein means that the aerosol that has filled the first chamber part 26A is then inevitably pushed into the second chamber part 26B communicating with the first chamber part 26A.

In the flavor dispenser apparatus 1B according to this embodiment, rather than introducing vaporized aerosol-generating liquid and air directly into the second chamber part 26B with a large diameter, the vaporized aerosol-generating liquid and air are mixed in advance in the first chamber part 26A with a small diameter (volume). In this way in which vaporized aerosol-generating liquid and air are mixed in advance in the first chamber part 26A with a small diameter (volume), after which the generated aerosol is introduced into the second chamber part 26B with a large diameter (volume), an aerosol with a uniform and high concentration can be generated.

While embodiments of the flavor dispenser apparatus according to the present invention have been described above, the flavor dispenser apparatus according to the present invention is not limited to the embodiments described above and various modifications may be made. Various embodiments and variation examples described above may also be combined as required.

REFERENCE SIGNS LIST

1 Flavor dispenser apparatus
10 Housing
11 Sound component
12 Operation unit
13 Light-emitting element
14 Control board
15 Storage part
16 Liquid delivery unit
17 Heating unit
18 Flavor cartridge
19 Flavor source holding part
20 Battery
21 Aerosol-pumping unit
22 Heater
23 Heating pipe
26 Chamber
28 Liquid delivery pump
29 Diaphragm pump
30 Dispenser nozzle
31 Aerosol outlet port
35 Pneumatic transport hose
40 Cradle

The invention claimed is:

1. A flavor dispenser apparatus comprising:
a storage part storing an aerosol-generating liquid;
a heating unit having a heater that heats the aerosol-generating liquid and generating an aerosol by atomizing the aerosol-generating liquid;
a liquid delivery unit delivering the aerosol-generating liquid stored in the storage part to the heating unit;
an aerosol passage for the aerosol generated in the heating unit to flow therethrough, the aerosol passage having an aerosol outlet port at a distal end thereof for discharging the aerosol to outside;
a flavor source holding part provided at an intermediate point in the aerosol passage and holding a flavor source so as to allow passage of the aerosol flowing through the aerosol passage; and
an aerosol-pumping unit transporting the aerosol generated in the heating unit through the aerosol passage toward the flavor source holding part and causing the aerosol to pass through a flavor source in the flavor source holding part as well as causing the aerosol flavored by the flavor source to be discharged from the aerosol outlet port.

2. The flavor dispenser apparatus according to claim 1, wherein the aerosol-pumping unit includes a pump or a tank for pneumatic transport of the aerosol generated in the heating unit through the aerosol passage toward the flavor source holding part.

3. The flavor dispenser apparatus according to claim 1, wherein the aerosol-generating liquid has a vapor pressure of 6.0 kPa (20° C.) or less.

4. The flavor dispenser apparatus according to claim 1, wherein the flavor source includes a solid flavor material.

5. The flavor dispenser apparatus according to claim 4, wherein the flavor source is a cartridge that includes a flavor case containing a solid flavor material therein and allowing an aerosol to pass therethrough and that is removably mounted in the flavor source holding part.

6. The flavor dispenser apparatus according to claim 5, wherein the flavor case is made of a transparent or translucent material.

7. The flavor dispenser apparatus according to claim 5, wherein the flavor case has, at least in part, a mesh structure or a porous structure.

8. The flavor dispenser apparatus according to claim 5, wherein the flavor source is mounted in the flavor source holding part in a manner visible from outside.

9. The flavor dispenser apparatus according to claim 1, further comprising
a hand-held housing, as well as a dispenser nozzle for dispensing an aerosol flavored by the flavor source into dishware,
the dispenser nozzle having at a distal end thereof the aerosol outlet port formed.

10. The flavor dispenser apparatus according to claim 9, wherein
the flavor source is a cartridge that includes a flavor case containing a solid flavor material therein and allowing an aerosol to pass therethrough and that is removably mounted in the flavor source holding part, and wherein
the housing is provided with a transparent window that makes the flavor source, mounted in the flavor source holding part, visible from outside.

11. The flavor dispenser apparatus according to claim 1, further comprising
a stationary housing having in an upper part thereof the aerosol outlet port, with a tubular wall standing in an upper part of the housing to divide an aerosol storage part, which stores an aerosol discharged from the aerosol outlet port, from a lateral ambient space of this aerosol storage part.

12. The flavor dispenser apparatus according to claim 2, wherein the aerosol-generating liquid has a vapor pressure of 6.0 kPa (20° C.) or less.

13. The flavor dispenser apparatus according to claim 2, wherein the flavor source includes a solid flavor material.

14. The flavor dispenser apparatus according to claim 3, wherein the flavor source includes a solid flavor material.

* * * * *